US010413620B2

(12) United States Patent
Pomper et al.

(10) Patent No.: US 10,413,620 B2
(45) Date of Patent: *Sep. 17, 2019

(54) LIGHT-EMITTING VERSIONS OF THE MONOCLONAL ANTIBODY TO C3D (MAB 3D29) FOR IMAGING

(71) Applicants: The Regents of the University of Colorado, a body corporate, Denver, CO (US); The Johns Hopkins University, Baltimore, MD (US)

(72) Inventors: Martin G. Pomper, Baltimore, MD (US); Catherine A. Foss, Baltimore, MD (US); Joshua M. Thurman, Aurora, CO (US); V. Michael Holers, Aurora, CO (US)

(73) Assignees: The Regents of the University of Colorado, a body corporate, Aurora, CO (US); The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/511,597

(22) PCT Filed: Sep. 15, 2015

(86) PCT No.: PCT/US2015/050232
§ 371 (c)(1),
(2) Date: Mar. 15, 2017

(87) PCT Pub. No.: WO2016/044300
PCT Pub. Date: Mar. 24, 2016

(65) Prior Publication Data
US 2017/0290930 A1 Oct. 12, 2017
US 2019/0240355 A9 Aug. 8, 2019

Related U.S. Application Data

(63) Continuation-in-part of application No. 14/624,347, filed on Feb. 17, 2015, now Pat. No. 9,259,488, which is a continuation of application No. PCT/US2013/055400, filed on Aug. 16, 2013.

(60) Provisional application No. 62/050,568, filed on Sep. 15, 2014, provisional application No. 61/684,691, filed on Aug. 17, 2012.

(51) Int. Cl.
*A61K 49/00* (2006.01)
*A61K 51/10* (2006.01)
*G01N 33/569* (2006.01)
*C07K 16/18* (2006.01)
*G01N 33/534* (2006.01)

(52) U.S. Cl.
CPC ...... *A61K 49/0058* (2013.01); *A61K 49/0043* (2013.01); *A61K 51/1009* (2013.01); *A61K 51/1018* (2013.01); *C07K 16/18* (2013.01); *G01N 33/5695* (2013.01); *C07K 2317/92* (2013.01); *G01N 33/534* (2013.01); *G01N 2469/10* (2013.01)

(58) Field of Classification Search
None
See application file for complete search history.

(56) References Cited

FOREIGN PATENT DOCUMENTS

WO WO 2014/028865 A1 2/2014

OTHER PUBLICATIONS

Thurman et al. 2013 (Detection of complement activation using monoclonal antibodies against C3d; The Journal of Clinical Investigation; 123(5):2218-2230) (Year: 2013).*
Baba et al. 1990 (Complement Activation in Pulmonary Tuberculosis; Tubercle 71:103-107). (Year: 1990).*
McKay et al. 1981 (A comparison of fluorescein isothiocyanate and lissamine rhodamine (RB200) as labels for antibody in the fluorescent antibody technique; Immunology 43: 591). (Year: 1981).*
Olafsen et al. 2010 (Antibody Vectors for Imaging; Seminars in Nuclear Medicine 40:167-181). (Year: 2010).*
Ahmad, et al., "Diagnosis of tuberculosis by using ELISA to detect 38kDa mycobacterial antigen in the patents," Immunology, Dec. 31, 1995, pp. 155-160.
Baba et al, "Complement activation in pulmonary tuberculosis," Tubercle, Longman Group UK Ltd, Harlow GB, vol. 71, No. 2, Jun. 1, 1990, pp. 103-107.
Thurman et al, "Detection of complement activation using monoclonal antibodies against C3d," Journal of Clinical Investigation, vol. 123, No. 5, May 1, 2013, pp. 2218-2230.
Extended European Search Report, European Application No. 15841341.9, dated Apr. 18, 2017, 10 pages.

* cited by examiner

*Primary Examiner* — Mary Maille Lyons
(74) *Attorney, Agent, or Firm* — Stanek Lemon Crouse & Meeks, PA

(57) ABSTRACT

The presently disclosed subject matter provides compositions and kits comprising light-emitting versions of the monoclonal antibody to C3d (mAB 3d29) for imaging and methods of use thereof for detecting infectious and inflammatory cells in vivo. The presently disclosed subject matter also provides methods for detecting and/or monitoring a *Mycobacterium tuberculosis* (*M. tuberculosis*) infection in a subject, as well as methods of treating a *M. tuberculosis* infection in a subject.

21 Claims, 12 Drawing Sheets

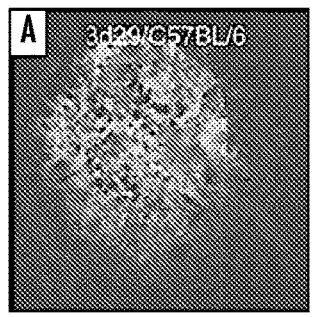 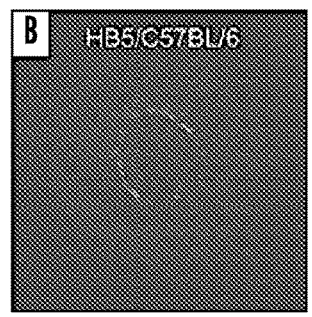 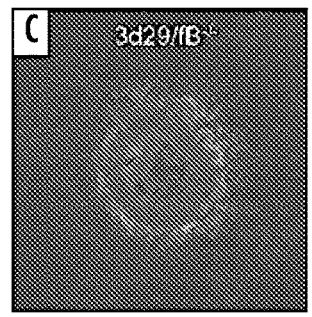
FIG. 10A  FIG. 10B  FIG. 10C
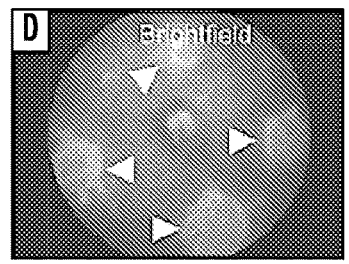 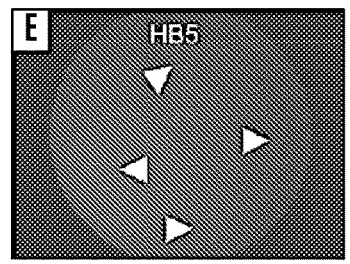
FIG. 10D  FIG. 10E
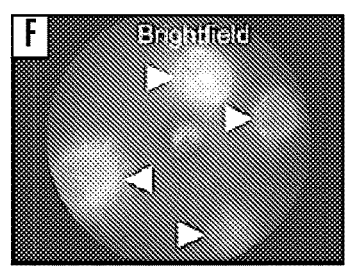 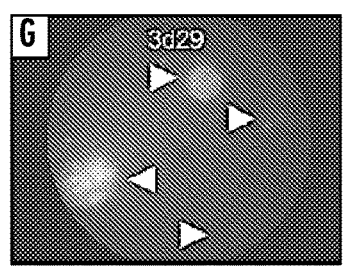
FIG. 10F  FIG. 10G

LIGHT-EMITTING VERSIONS OF THE MONOCLONAL ANTIBODY TO C3D (MAB 3D29) FOR IMAGING

CROSS-REFERENCE TO RELATED APPLICATIONS

This application is a 35 U.S.C. § 371 U.S. national phase entry of International Application No. PCT/US2015/0502 having an international filing date of Sep. 15, 2015, which claims the benefit of U.S. Provisional Patent Application No. 62/050,568 filed on Sep. 15, 2014. This application also claims priority to U.S. patent application Ser. No. 14/624, 347, filed on Feb. 17, 2015, now U.S. Pat. No. 9,259,488, which is a continuation application of International Application No. PCT/US2013/055400 having an international filing date of Aug. 16, 2013, which claims the benefit of U.S. Provisional Patent Application No. 61/684,691 filed on. Aug. 17, 2012. The contents of each of which are hereby incorporated herein by reference in their entireties.

BACKGROUND

*Mycobacterium tuberculosis* is a pathogen that evades the host immune system by living within alveolar and peripheral macrophages. Host evasion is partially accomplished by M. tb coating itself with complement fragment 3d (C3d), which directs it for phagocytosis by the host macrophage and inhibits the full Complement response. Because C3d is generated only during specific types of inflammatory events and binds its target rapidly, C3d serves as an excellent biomarker for imaging infections and other specific inflammatory events.

The complement system is an important arm of the innate immune system, providing critical protection against invasive pathogens (Ricklin et al., 2001)) and contributing to the pathogenesis of numerous autoimmune and inflammatory diseases (Walport, 2001). During the course of complement activation, the C3 protein undergoes proteolytic cleavage at several different sites (FIG. 1). The cleavage fragments are fixed to nearby tissues through a covalent linkage originating from the thioester site on C3 with hydroxyl or primary amine groups on acceptor surfaces (3-5). Thus, the deposition of C3 fragments on tissue surfaces constitutes a durable signal of tissue inflammation. For this reason, tissue-bound C3 fragments are commonly used clinically and experimentally as biomarkers of immune activation. Renal biopsies from patients with glomerulonephritis, for example, are routinely immunostained for C3 fragments, and the detection of glomerular C3 fragments serves as a sensitive and robust indicator of disease activity (Schulze et al., 1993). C3 deposition has also been recognized to occur in all stages of age-related macular degeneration (Hageman et al., 2001).

Because tissue-bound C3 fragments are associated with local inflammation, they also have been exploited as addressable binding ligands for targeted therapeutics and diagnostic agents in several tissues, including the kidneys, the heart, the brain, and the eyes (Atkinson et al., 2005; Serkova et al., 2010; Sargsyan et al., 2012; Rohrer et al., 2009; Rohrer et al., 2012). These targeted agents have employed recombinant forms of complement receptor 2 (CR2), a protein that can discriminate between intact C3 in the plasma and tissue-bound C3 fragments. The rationale for this approach is that systemically administered agents can be delivered to sites of inflammation through their affinity with the iC3b and C3d fragments. By directing therapeutic agents to molecular targets, one can achieve a high degree of local activity with the drug while minimizing its systemic side effects (Webb, 2011). Previous studies also have used a CR2-targeted contrast agent to detect tissue-bound C3 fragments and renal disease activity by MRI (Serkova et al., 2010; Sargsyan et al., 2012). Although specific for the cleaved forms of C3, CR2-targeted agents probably bind these fragments with a relatively low affinity (reported values range from 1 to 10 µM at physiologic ionic strength) (Guthridge et al., 2001; Isenman et al., 2010; Dempsey et al., 1996). Higher-affinity targeting vectors for epitopes on the cleaved forms of C3 could potentially deliver therapeutic and diagnostic agents to sites of inflammation with even greater efficiency, durability, and specificity.

Informative monoclonal antibodies (mAbs) against tissue-bound C3 fragments have many biomedical applications. They could be used as in vivo delivery vehicles for new therapeutic and diagnostic agents. They also could potentially modulate the biologic functions of the C3 fragments. Such antibodies also could be useful for identifying specific C3 fragments (e.g., C3b, iC3b, C3dg, and C3d) and quantifying their relative abundance. There are, however, several barriers to the generation of such antibodies by standard methods. Like CR2, the antibodies must recognize epitopes of cleaved C3 that are not exposed on intact C3 (which circulates at a concentration of 1 to 2 mg/ml). This is feasible, however, since internal regions of C3d (and also iC3b and C3dg) are exposed by conformational changes in C3 during its activation and subsequent proteolytic processing of its fragments (Janssen et al., 2006). Another difficulty is that standard methods for generating and cloning hybridomas may expose the hybridoma cells to C3 and C3 fragments in serum-containing media, or to C3 synthesized by cells, such as macrophages, that are used in the cultures. C3 and C3 fragments in the media could mask positive hybridoma clones or affect the growth of such clones through engagement of the B cell receptors.

SUMMARY

In an aspect, the presently disclosed subject matter provides a method for detecting and/or monitoring a *Mycobacterium tuberculosis* (*M. tuberculosis*) infection in a subject, the method comprising: (a) administering to a subject an effective amount of a monoclonal antibody or antibody derivative which binds to C3d in the subject, wherein the monoclonal antibody or antibody derivative is conjugated to an imaging tag; and (b) detecting a signal generated by the imaging tag to detect and/or monitor the location of the *M. tuberculosis* infection in the subject. The monoclonal antibody, which binds to C3d in the subject was deposited in the American Type Culture Collection (ATCC), 10801 University Blvd, Manassas, Va. 20110 on May 26, 2010 and designated PTA-10998, PTA-10999, or PTA-11000; on Jun. 3, 2010 and designated PTA-11010, PTA-11011 or PTA-11012; and on Jun. 9, 2010 and designated PTA-11025, PTA-11026 or PTA-11027.

In another aspect, the presently disclosed subject matter provides for the use of a monoclonal antibody or antibody derivative which binds to C3d for detecting and/or monitoring a *M. tuberculosis* infection in a subject, wherein the antibody or antibody derivative is conjugated to an imaging tag.

In yet another aspect, the presently disclosed subject matter provides for the use of antibody 3d29 or a derivative thereof for detecting and/or monitoring a *M. tuberculosis* infection in a subject, wherein the antibody or antibody derivative is conjugated to an imaging tag.

In some embodiments, the antibody or antibody derivative comprises 3d29 or a derivative thereof. In some embodiments, the antibody or antibody derivative (e.g., 3d29 or a derivative thereof) binds to infected tissue in the subject. In some embodiments, the infected tissue comprises inflamed tissue. In some embodiments, the infected tissue is selected from the group consisting of lung, spleen, and any other extrapulmonary infected tissue. In some embodiments, the antibody or antibody derivative co-localizes with alveolar and peripheral phagocytes in *M. tuberculosis* infected lung sections in the subject and/or co-localizes with aggregates of macrophages in the lungs of infected subjects. In some embodiments, the imaging tag is a fluorescent tag and/or a radiolabel. In some embodiments, the imaging tag comprises any radioiodine nuclide. In some embodiments, the imaging tag comprises $^{125}$I, $^{123}$I, $^{124}$I, or $^{131}$I. In some embodiments, the imaging tag comprises LISSAMINE, IRDye680RD or IRDye800CW.

In some embodiments, the step of detecting the signal comprises performing an imaging method selected from the group consisting of computed tomography (CT), fluorescence imaging, and single-photon emission computed tomography (SPECT), positron emission tomography (PET) and combinations thereof.

In some embodiments, the step of administering comprises injecting the antibody or antibody derivative into the subject. In some embodiments, injecting comprises intravenous or intraperitoneal injection.

In some embodiments, the method further comprises treating the subject for *M. tuberculosis* infection. In some embodiments, treating comprises administering to the subject an effective amount of an antibiotic agent, an anti-inflammatory agent, or a combination thereof. In some embodiments, the subject is human.

In another aspect, the presently disclosed subject matter provides a method of treating a *M. tuberculosis* infection in a subject in need thereof, the method comprising: (a) administering to a subject an effective amount of a monoclonal antibody or antibody derivative which binds to C3d, wherein the monoclonal antibody or antibody derivative is conjugated to an imaging tag, and wherein the antibody or antibody derivative binds to infected tissue in the subject; (b) detecting a signal generated by the imaging tag to detect and/or monitor the location of the *M. tuberculosis* infection in the subject; and (c) administering to the subject an effective amount of an antibiotic agent, an anti-inflammatory agent, or a combination thereof. In some embodiments, the infected tissue comprises inflamed tissue. In some embodiments, the antibiotic agent and/or anti-inflammatory agent are administered to the location of the *M. tuberculosis* infection in the subject. In some embodiments, the antibiotic agent and/or anti-inflammatory agent are administered to the location of the inflammation in the subject. In some embodiments, the subject is human.

In one aspect, the presently disclosed subject matter provides a purified monoclonal antibody or antibody derivative which binds to a complement C3 activation fragment and is capable of imaging the complement C3 activation fragment in vivo when bound to an imaging tag. In a particular embodiment, the imaging tag is a fluorescent tag and/or a radiolabel.

In certain aspects, the presently disclosed subject matter provides an imaging kit for visualizing a complement C3 activation fragment comprising the antibody or antibody derivative.

In other aspects, the presently disclosed subject matter provides a method for detecting infection or inflammation in a subject, the method comprising administering to the subject an antibody or antibody derivative linked to a labeling substance, wherein the antibody or antibody derivative binds to a complement C3 activation fragment, and wherein binding to the complement C3 activation fragment means that the subject has an infection or inflammation.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 1:
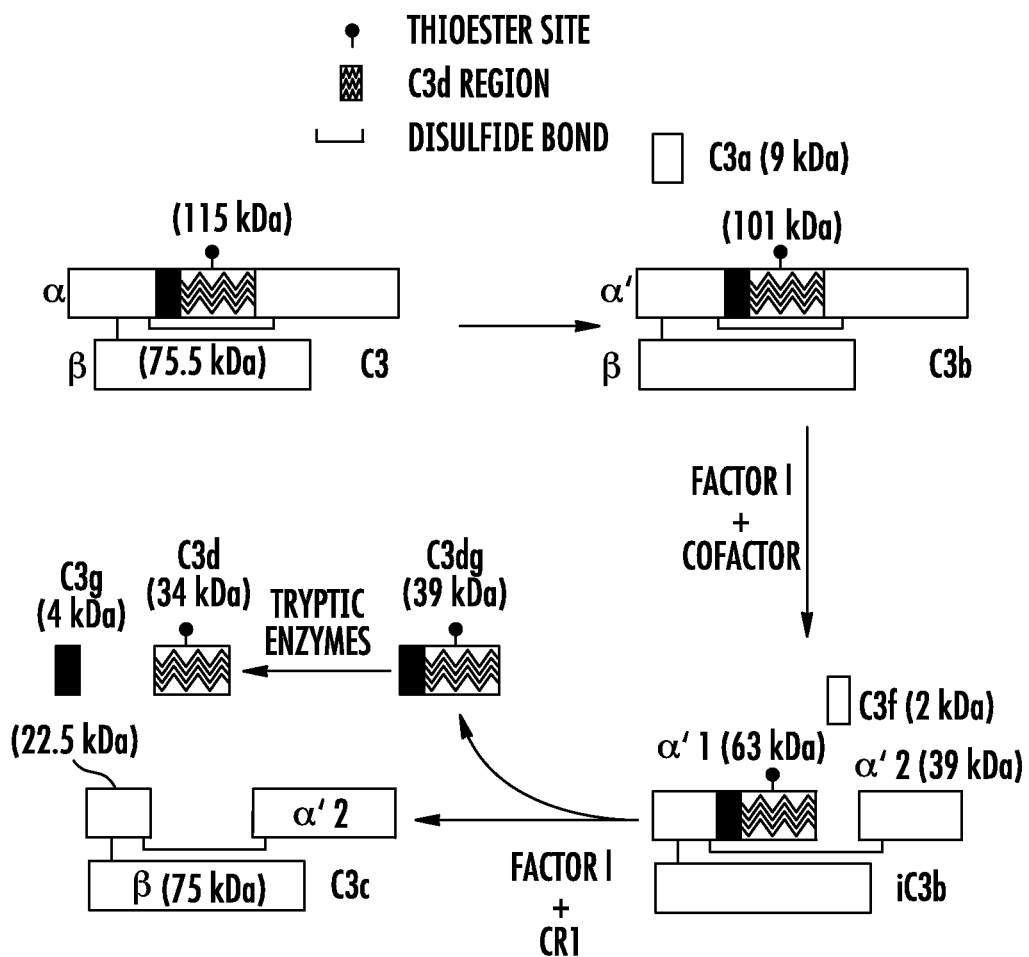
Figure 2A:
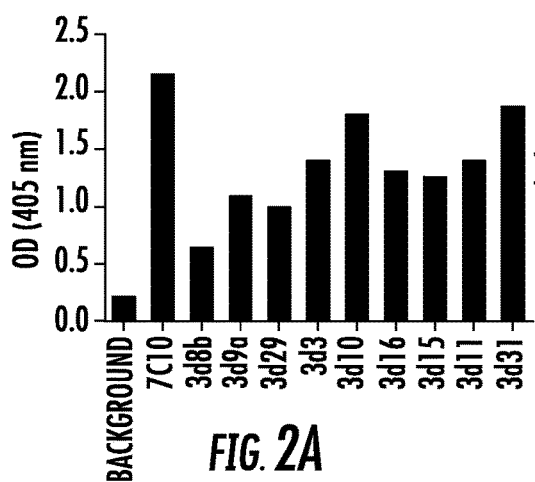
Figure 2B:
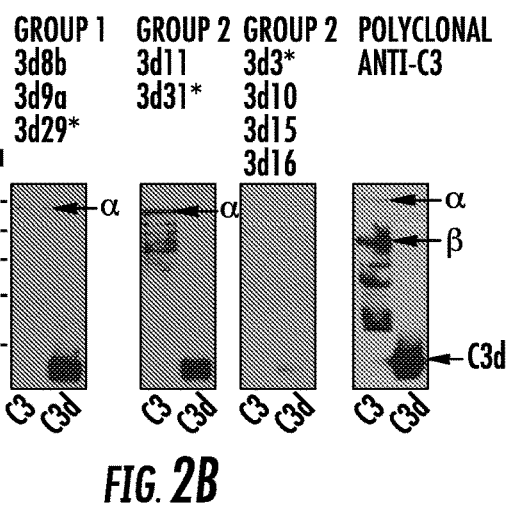
Figure 2C:
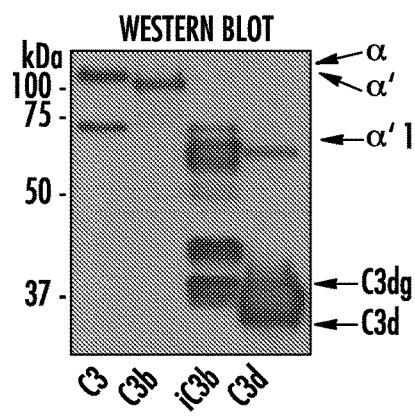
Figure 2D:
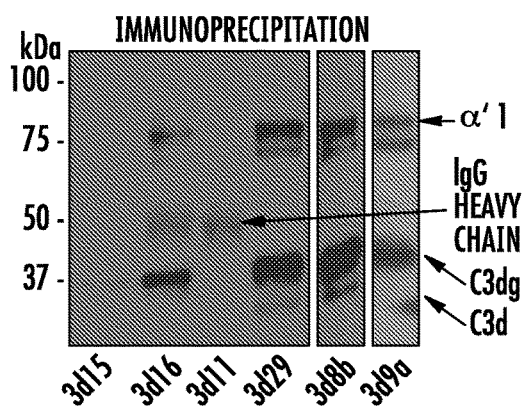
Figure 3:
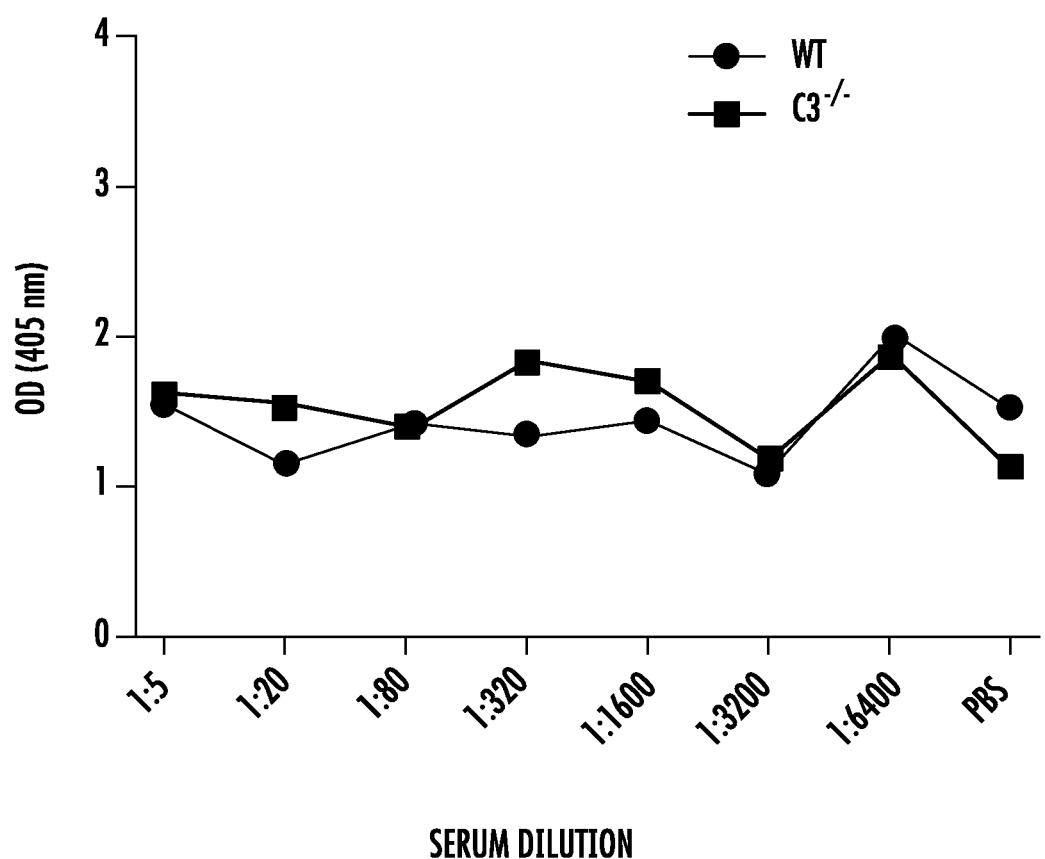
Figure 4:
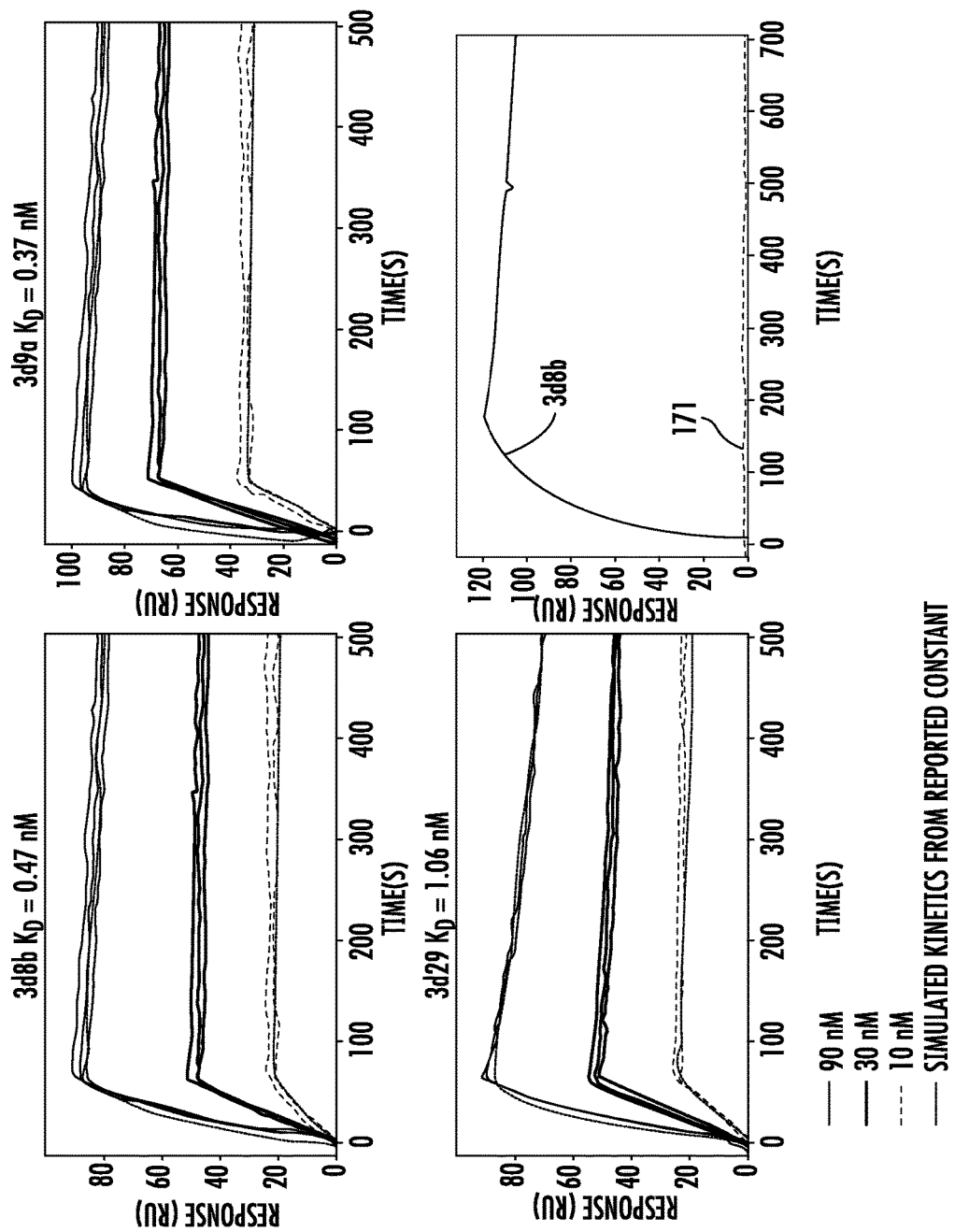
Figure 5A:
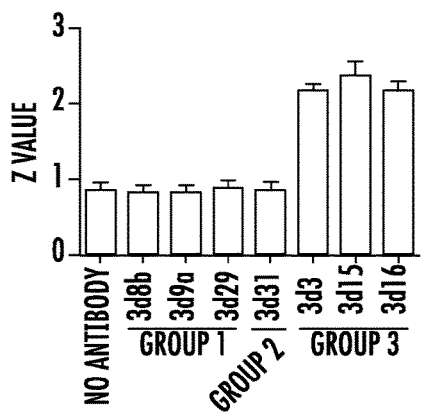
Figure 5B:
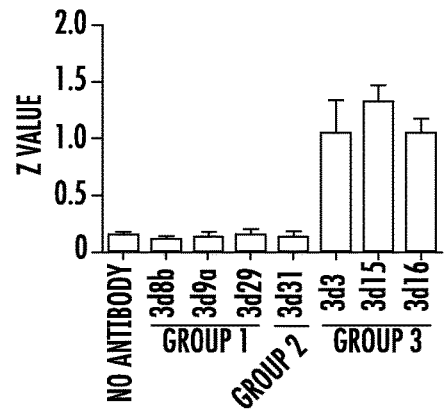
Figure 5C:
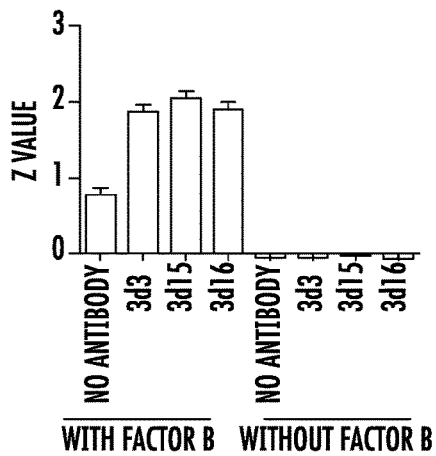
Figure 5D:
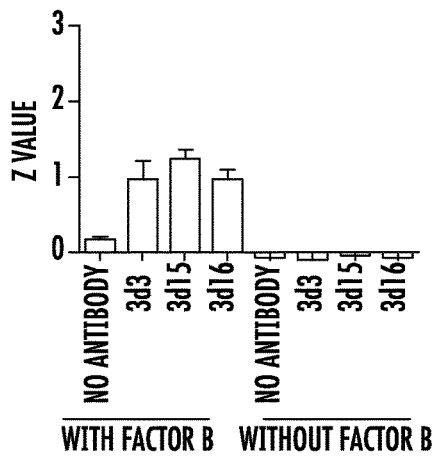
Figure 5E:
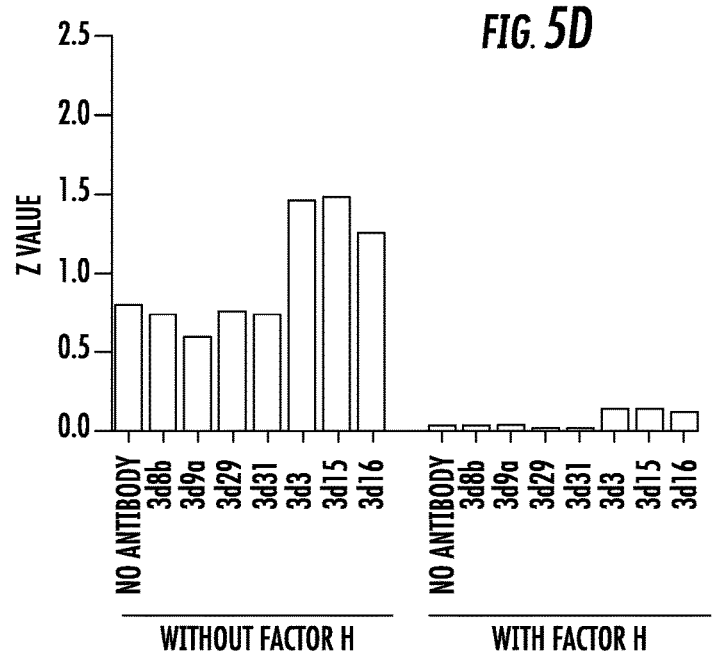
Figure 6A:
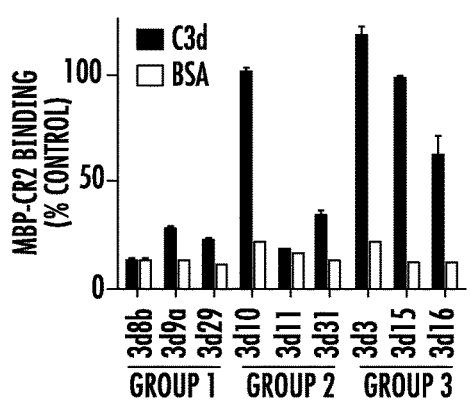
Figure 6B:
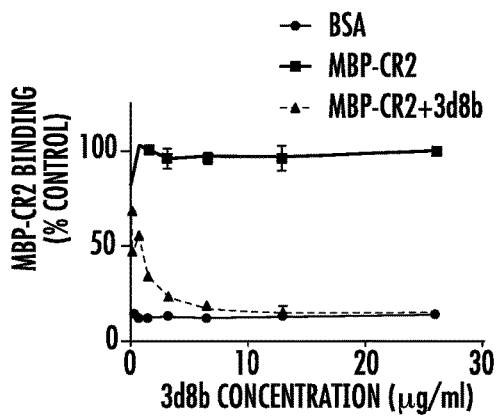
Figure 6C:
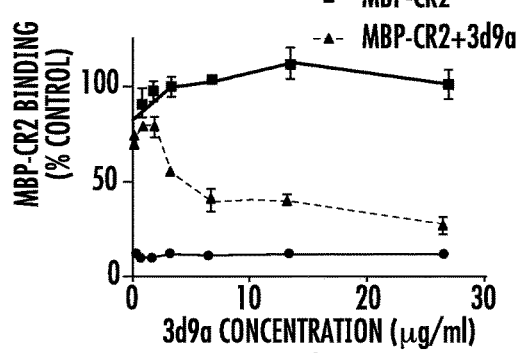
Figure 6D:
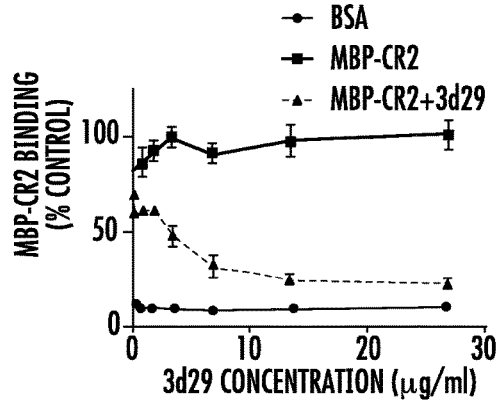
Figure 6E:
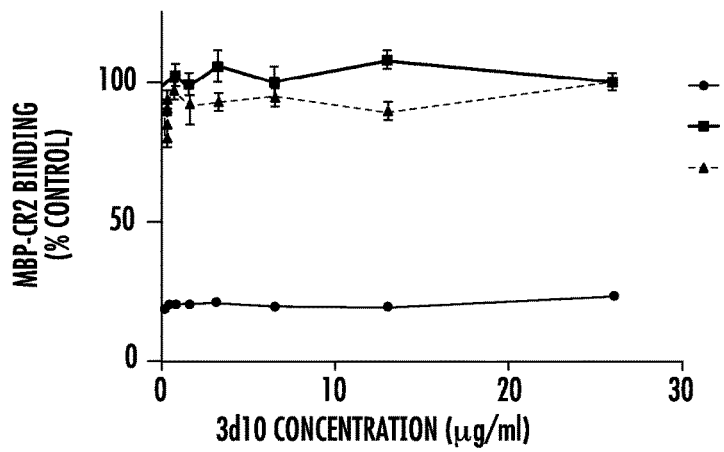
Figure 7A:
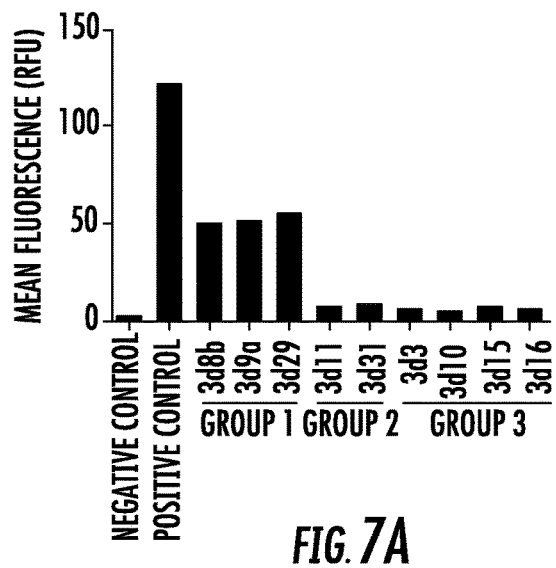
Figure 7B:
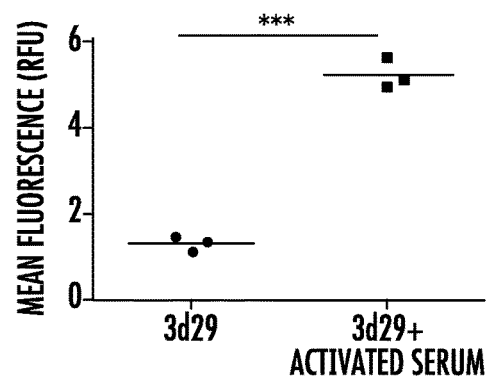
Figure 7C:
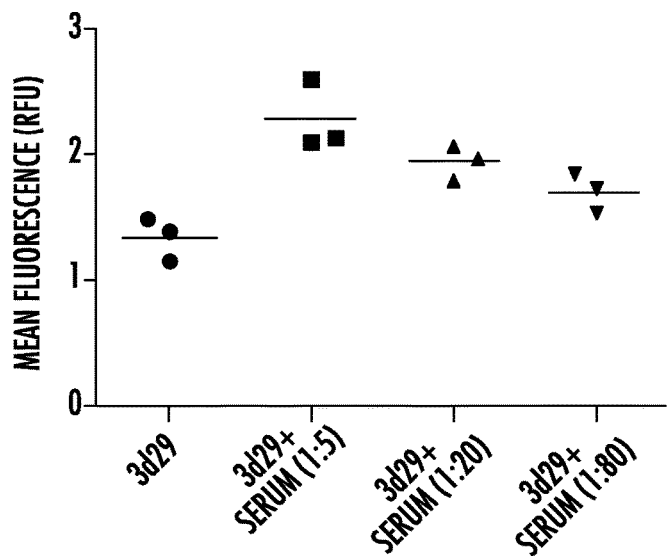
Figure 8A:
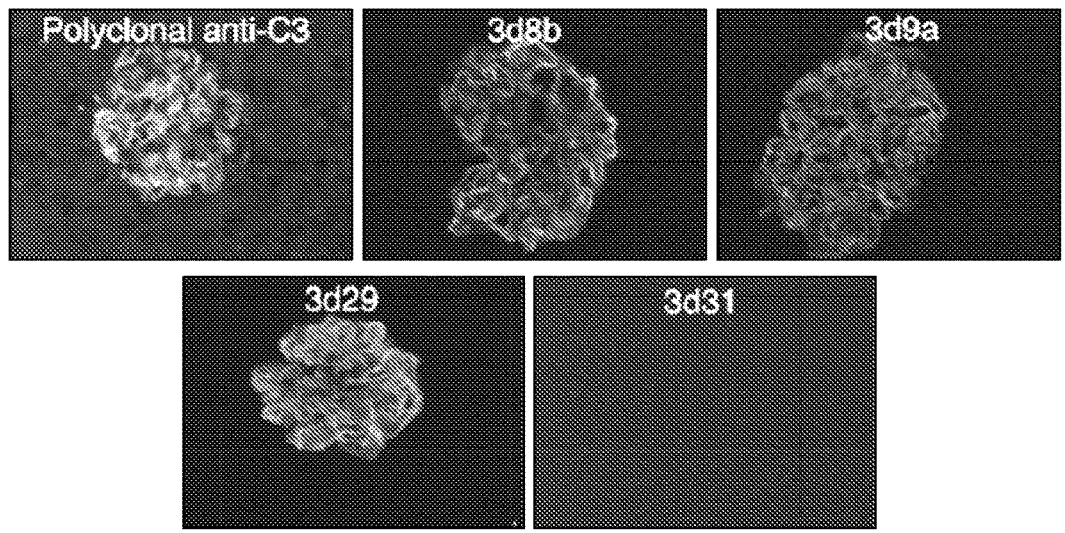
Figure 8B:
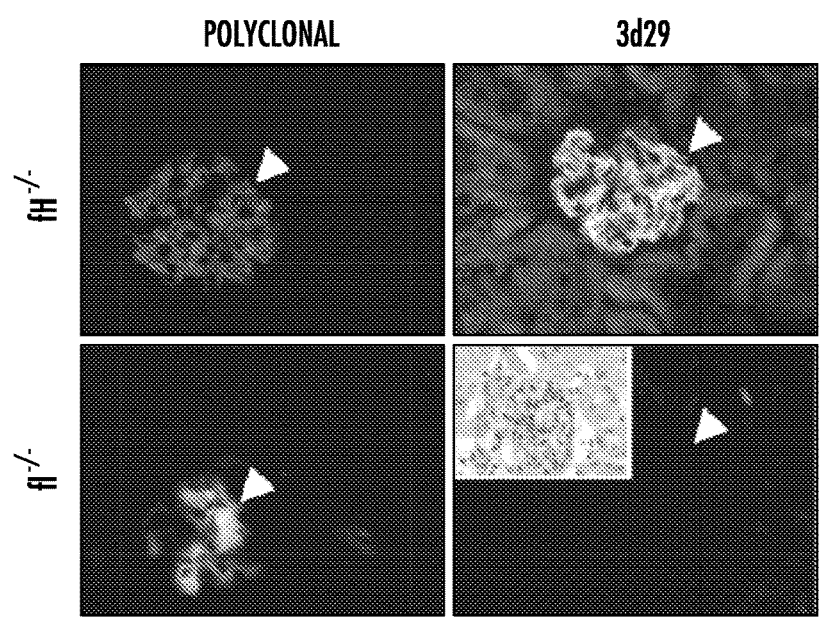
Figure 9A:
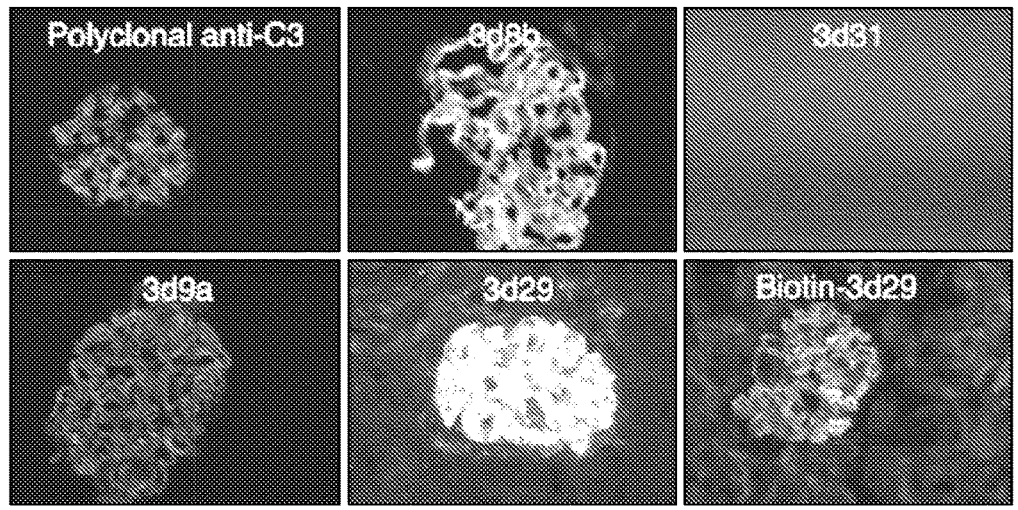
Figure 9B:
Figure 11A:
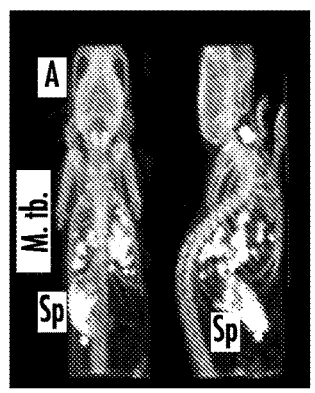
Figure 11B:
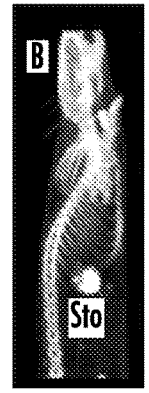
Figure 11C:
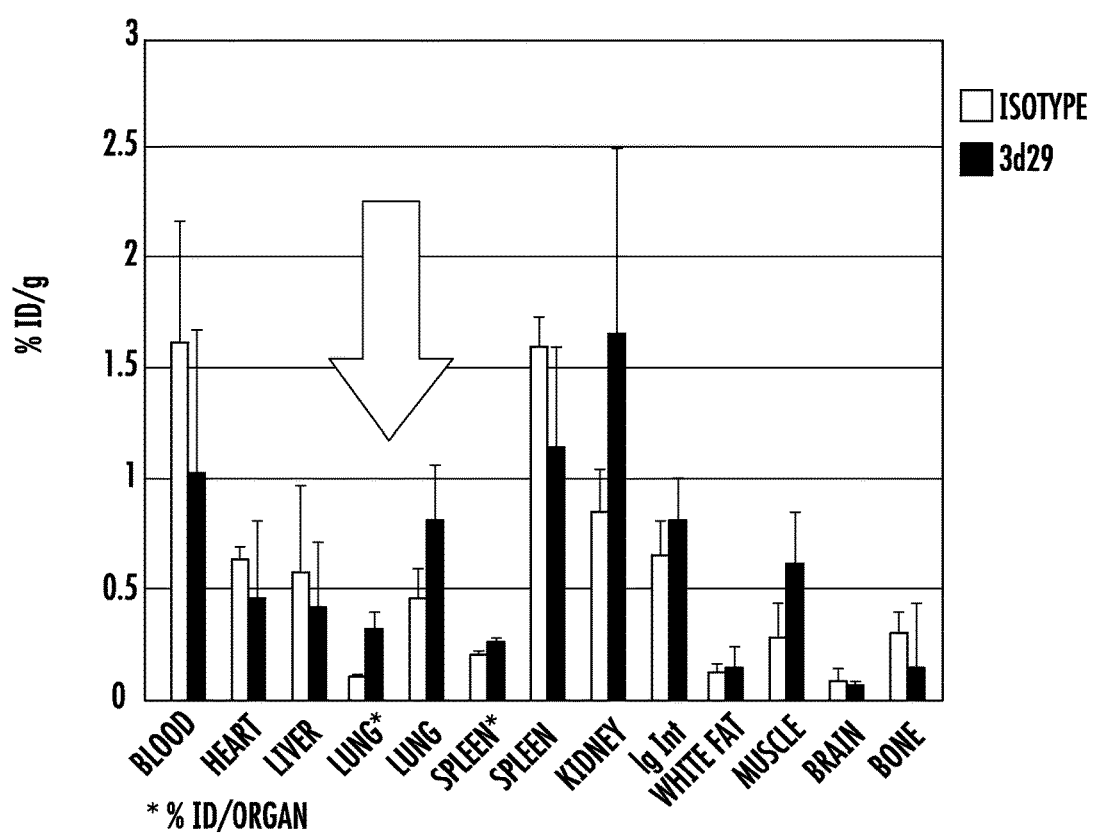
Figure 11D:
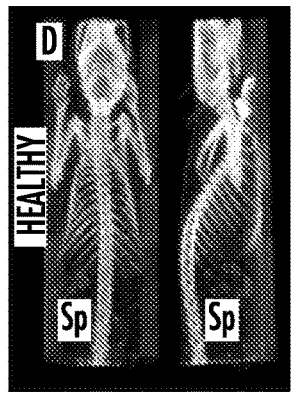
Figure 11E:
Figure 11F:

Having thus described the presently disclosed subject matter in general terms, reference will now be made to the accompanying Figures, which are not necessarily drawn to scale, and wherein:

FIG. 1 shows metabolism of C3 to iC3b and C3d during complement activation. During complement activation, the C3 protein undergoes proteolytic cleavage at several locations. The C3d domain is present within the C3, C3b, and iC3b molecules. However, conformational changes in the 3D structure of C3 expose C3d epitopes during cleavage of the C3 molecule;

FIG. 2A, FIG. 2B, FIG. 2C, and FIG. 2D show the generation of mAbs that recognize C3 activation fragments. Anti-human C3d hybridomas were generated: FIG. 2A shows the hybridomas were screened against recombinant human C3d by ELISA, and 9 of the clones bound to the protein (clone 7C10 was used as a positive control, and the remaining clones were newly identified); FIG. 2B shows reactivity of the clones against reduced intact human C3 and recombinant human C3d by Western blot analysis was tested. Three patterns of reactivity were seen: Group 1 clones bound strongly to reduced C3d; Group 2 clones bound to the α chain of reduced intact C3; and Group 3 clones did not bind well to either moiety. The asterisk denotes the mAb whose results are shown. The rightmost blot shows the result using a polyclonal antibody against mouse C3. The lower molecular weight bands detected by the mAbs in the C3 samples are likely contaminants; FIG. 2C shows clone 3d11 recognized all of the human C3 α chain fragments by Western blot analysis. The appearance of the α, α', α'1, C3dg, and C3d fragments from purified human proteins are shown. The lower molecular weight bands detected in the C3 and iC3b samples are likely contaminants; and FIG. 2D shows immunoprecipitation of C3 fragments in mouse serum demonstrated that the Group 1 clones recognize the iC3b form (α'1 chain) and C3dg, but do not bind to the C3 and C3b (α and α' chains). Clone 3d16 demonstrated some binding to the iC3b and C3dg fragments. The results using 3d8b were from a separate gel. The immunoprecipitated proteins were visualized by Western blot analysis with mAb 3d11 under reducing conditions;

FIG. 3 shows that proteins in mouse serum do not reduce the binding of 3 d29 to platebound C3d. The anti-C3d mAbs were tested in a C3d ELISA in which increasing concentrations of serum from wild-type and C3-deficient (C3−/−) mice were added to the reactions. Binding of the anti-C3d mAbs was not reduced by wild-type or C3−/− serum in any of the dilutions tested. The results for mAb 3d29 are shown;

FIG. 4 shows surface plasmon resonance of clones 3d8b, 3d9a, and 3d29 against recombinant human C3d demonstrate high-affinity binding. Surface plasmon resonance was performed using recombinant human C3d. The protein was immobilized on a CM5 chip (100 RU), and samples containing variable concentrations of the antibodies (90, 30, or 10 nM) were added. The data were fitted using a 1:1 Langmuir binding model and equilibrium dissociation constants (KD) were calculated. mAb 171 was used as a negative control, and the results of binding with mAb 171 (blue line) were compared with the results using mAb and mAb 3d8b, both at 90 nM. The anti-C3d mAbs demonstrated high-affinity binding, and the KDs are shown for each mAb studied;

FIG. 5A, FIG. 5B, FIG. 5C, FIG. 5D, and FIG. 5E show that clones 3d3, 3d15, and 3d16 stabilize C3 convertase on sheep erythrocytes. Sheep erythrocytes were sensitized with antibody and opsonized with human C3b. They were then treated with factor B, factor D, and properdin to generate AP C3 convertases (C3bBbP) on the cell surfaces. One microgram of antibody was added to a 150-µl reaction mix, and the cells were used immediately as shown in FIG. 5A and FIG. 5C, or incubated for 2 hours as shown in FIG. 5B and FIG. 5D. n=4-6 for each condition: FIG. 5A shows when guinea pig serum was added to the erythrocytes as a source of MAC and the average number of lytic sites was calculated (Z value), cells treated with clones 3d3, 3d15, and 3d16 demonstrated a greater MAC formation than control-treated cells; FIG. 5B shows when the cells were incubated 2 hours prior to addition of the guinea pig serum, the same 3 clones showed greater Z values, indicating that these clones stabilize the C3 convertase on the cell surface; FIG. 5C and FIG. 5D show the experiment was repeated for clones 3d3, 3d15, and 3d16 in the presence or absence of factor B. In the absence of factor B, MAC formation was eliminated, demonstrating that the reaction required formation of the alternative pathway C3 convertase; and FIG. 5E shows the same reaction was repeated but with the addition of 400 ng of factor H. None of the antibodies tested interfered with the ability of factor H to dissociate the C3 convertase and prevent MAC formation. This experiment was performed in duplicate, and the mean of these results is shown;

FIG. 6A, FIG. 6B, FIG. 6C, FIG. 6D, and FIG. 6E show inhibition of the CR2-C3d interaction by anti-C3d mAbs: FIG. 6A shows a competition ELISA was performed to test whether the anti-C3d mAbs interfere with the binding of a recombinant construct of the 2 N-terminal domains of CR2 (MBP-CR2) and plate-bound C3d. The percentage of MBP-CR2 binding (y-axis) (kept at a constant concentration of 10 µg/ml) to C3d was determined in the presence of individual anti-C3d mAbs (x-axis) at a concentration of 26 µg/ml. Values are normalized to a positive control in which C3d-coated wells were incubated with MBP-CR2 in the absence of anti-C3d mAbs (not shown). Also shown for each sample is a negative control in which the wells were coated with BSA instead of C3d; FIG. 6B, FIG. 6C, and FIG. 6D show capacity of the Group 1 mAbs (3d8b, 3d9a, and 3d29) to block MBP-CR2 binding to plate-bound C3d at mAb concentrations ranging from 1.625 to 26 µg/ml; and FIG. 6E shows that 3d10 did not block the binding of CR2 to plate-bound C3d over the same concentration range;

FIG. 7A, FIG. 7B, and FIG. 7C show clones 3d8b, 3d9a, and 3d29 bind to mouse C3 fragments generated in vitro: FIG. 7A shows normal mouse serum was activated on zymosan particles, and binding of the antibodies to the C3-opsonized particles was tested. The opsonized particles were incubated with 1 µg of each antibody, and bound antibody was detected by flow cytometry. Polyclonal anti-mouse C3 was used as a positive control. Clones 3d8b, 3d9, and 3d29 bound to the opsonized particles. This assay was repeated on separate occasions, and a representative result is shown; FIG. 7B shows zymosan particles were opsonized with C3 using normal mouse serum and were then incubated with biotinylated 3d29. Incubating 3d29 with the particles in the presence of the activated serum failed to reduce binding of 3d29 to the particle surface and actually increased binding. ***P<0.001; and FIG. 7C shows the addition of fresh mouse serum to the supernatant when the antibody was incubated with the particles did not reduce binding of biotinylated 3d29 to the particle surface;

FIG. 8A and FIG. 8B show that clones 3d8b, 3d9a, and 3d29 bind to mouse C3 fragments generated in vivo: FIG. 8A shows kidney tissue sections from factor H-deficient mice (fH−/−) were used to test binding of the antibodies to C3 tissue deposits. Factor H mice are known to have abundant deposition of C3 fragments along the glomerular capillaries without IgG at this location. This was confirmed by immunostaining with a polyclonal antibody against mouse C3. Kidney tissue sections were then incubated with 5 µg/ml of each clone. Clones 3d8b, 3d9, and 3d29 bound to the capillaries in a pattern identical to that of polyclonal anti-C3. The remaining 6 clones did not demonstrate substantive binding (the result for clone 3d31 is shown); and FIG. 8B shows kidneys from factor I-deficient (fI−/−) mice were immunostained with a polyclonal antibody against C3 and with mAb 3d29. The fI−/− mice cannot generate iC3b. The absence of glomerular staining in fI−/− mice by mAb 3d29 confirms that the mAb does not recognize C3b. Glomeruli are indicated with arrowheads. Original magnification, ×400 for all panels, including the inset;

FIG. 9A and FIG. 9B show that clones 3d8b, 3d9a, and 3d29 target tissue-bound C3 fragments after systemic in vivo injection: FIG. 9A shows factor H− deficient mice were injected with 0.5 mg of each antibody. After 24 hours the mice were sacrificed, and immunofluorescence microscopy was performed to detect glomerular IgG. Mice injected with clones 3d8b, 3d9, and 3d29 demonstrated IgG deposition along the capillary walls in a pattern indistinguishable from that of C3 deposition (as shown by control staining of a section with a polyclonal anti-C3 antibody). These mice do not have detectable C3 deposits along the tubules, and no IgG was seen in the tubulointerstitium. To confirm that the detection antibody was not binding to endogenous IgG, clone 3d29 was biotinylated and the experiment was repeated. Streptavidin-FITC was used to detect the injected antibody, and again, it could be seen along the capillary loops; and FIG. 9B shows wild-type C57BL/6 mice demonstrate C3 deposits along the basolateral aspect of the tubules. Unmanipulated C57BL/6 mice were injected with biotinylated 3d29 or with a biotinylated control antibody. The mice were sacrificed after 24 hours, and 3d29 was detected in the kidneys using strepatavidin-PE. The antibody was detected along the tubules in a pattern indistinguishable from the C3 deposits. Original magnification, ×400;

FIG. 10A, FIG. 10B, FIG. 10C, FIG. 10D, FIG. 10E, FIG. 10F, and FIG. 10G show clones 3d29 target tissue-bound C3 fragments in the retina in a model of CNV. Four laser spots in each eye were created by Argon laser photocoagulation: FIG. 10A shows FITC-3d29 strongly bound to CNV lesions in flat mounts made from wild-type mice; FIG. 10B shows low-intensity staining was observed for HB5, a control antibody, to the edge of the CNV lesions in flat mounts made from wild-type mice; FIG. 10C shows low-intensity staining of FITC-3d29 was observed in CNV lesions in flat mounts made from fB−/− mice; FIG. 10D shows bright-field image revealing 4 depigmented CNV lesions in a wild-type mouse; FIG. 10E shows fluorescence image of the same fundus demonstrating that no fluorescence is detectable in live CNV mice injected with 0.2 mg FITC-HB5; FIG. 10F shows bright-field image revealing 4 depigmented CNV lesions in a wild-type mouse injected with FITC-3d29; and FIG. 10G shows fluorescence image of the same fundus demonstrating that fluorescence is clearly detectable in live CNV mice injected with 0.2 mg FITC-3d29. Original magnification, ×630 for FIG. 10A, FIG. 10B, and FIG. 10C and resolution element ("resel") of approximately 4 µm for FIG. 10D, and FIG. 10E; and FIG. 11A, FIG. 11B, FIG. 11C, FIG. 11D, FIG. 11E, and FIG. 11F show: FIG. 11A shows coronal and sagittal views of [$^{125}$I]3d29 SPECT-CT after 24 h of uptake showing abundant focal pulmonary uptake as well as in spleen (Sp) and metabolized radioiodine in thyroid; FIG. 11B shows sagittal view of [$^{125}$I]isotype control uptake in an infected mouse after 24 hours of uptake. Only stomach (Sto) and thyroid uptake are visible; FIG. 11C shows ex vivo biodistribution of carrier-free [$^{125}$I]3d29 and [$^{125}$I]isotype in infected mice showing three-fold higher total lung uptake of 3d29 in infected mice; FIG. 11D shows coronal and sagittal [$^{125}$I]3d29 SPECT-CT in healthy mice after a 24 h uptake; FIG. 11E shows sagittal view of [$^{125}$I]isotype control uptake in an infected mouse after 24 hours of uptake; and FIG. 11F shows ex vivo microscopy showing co-localization of injected fluorescent 3d29 with CD68+ phagocytes in infected lungs (top panel) with only trace binding to luminal alveolar macrophages in a healthy mouse.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

In some embodiments, the presently disclosed subject matter provides compositions, methods and kits for imaging and therapy of infectious disease and inflammation. In other embodiments, the presently disclosed subject matter provides antibody and antibody derivatives (e g, minibodies, diabodies) for imaging a variety of infectious and inflammatory entities, such as experimental models of chronic bacterial infection, disseminated tuberculosis and rheumatoid arthritis. In still other embodiments, fluorescent or radiolabeled versions of antibody 3d29 are used in the presently disclosed methods. In further embodiments, fluorescent antibody is used for imaging in vivo or in cellulo or for fluorescence-activated cell sorting.

In some embodiments, the agents are capable of detecting infectious or inflammatory cells in vivo (the radioactive or near-infrared emitting versions) or in cellulo (the optical version). In other embodiments, this is the first time that complement has been imaged specifically in vivo for the purpose of studying infection or inflammation.

During complement activation the C3 protein is cleaved, and C3 activation fragments are covalently fixed to tissues. Tissue-bound C3 fragments are a durable biomarker of tissue inflammation, and these fragments have been exploited as addressable binding ligands for targeted therapeutics and diagnostic agents. Cross-reactive murine monoclonal antibodies against human and mouse C3d have been generated, the final C3 degradation fragment generated during complement activation. Three monoclonal antibodies (3d8b, 3d9a, and 3d29) that preferentially bind to the iC3b, C3dg, and C3d fragments in solution, but do not bind to intact C3 or C3b were generated. The same three clones also bind to tissue-bound C3 activation fragments when injected systemically. Using mouse models of renal and ocular disease, it was confirmed that, following systemic injection, the antibodies accumulated at sites of C3 fragment deposition within the glomerulus, the renal tubulointerstitium, and the posterior pole of the eye. To detect antibodies bound within the eye, optical imaging was used and accumulation of the antibodies within retinal lesions in a model of choroidal neovascularization (CNV) was observed.

The results demonstrate that imaging methods that use these antibodies provide a sensitive means of detecting and monitoring complement activation-associated tissue inflammation. It was found that [$^{125}$I]3d29 but not [$^{125}$I]isotype control SPECT-CT sensitively detects granulomas and inflamed spleen in infected mice. Healthy mice display minimal spleen uptake of [$^{125}$I]3d29 while [$^{125}$I]isotype signal is restricted to stomach and thyroid due to radioiodine metabolite (FIG. 11A, FIG. 11B, FIG. 11D, and FIG. 11E). Ex vivo biodistribution of low dose [$^{125}$I]3d29 and [$^{125}$I] isotype control in M. tb. infected mice showed a 3:1 elevation of 3d29 uptake in infected lungs over isotype (FIG. 11C). The focal nature of [$^{125}$I]3d29 binding to granulomas and inflamed spleen allow them to be clearly observed over blood pool and other less inflamed tissues. 3d29-LISSAMINE conjugate co-localizes with alveolar and peripheral phagocytes in M. tb infected lung sections while only trace uptake is detected in uninfected luminal alveoolar phagocytes (FIG. 11F). No binding of isotype conjugate was observed.

Novel methods have been used herein to develop 9 murine monoclonal antibodies against human C3d that cross-react with both mouse and cynomolgus C3d. Three of these high-affinity antibodies discriminate the cleaved forms of C3 from the intact C3 protein. Furthermore, the presently disclosed studies demonstrate that these antibodies can be used to target tissue sites of complement activation in vivo despite high levels of intact C3 in the circulation. Methods are reported herein that were used to develop these monoclonal antibodies against C3d and evidence is presented that these reagents target tissue-bound C3d in vivo.

The optimal treatment of chronic infections and autoimmune diseases requires methods for accurately detecting and localizing tissue inflammation. Complement C3 activation fragments are fixed to pathogens and to host cells during the immune response, and thus can serve as biomarkers of ongoing inflammation. Several probes have been developed that detect tissue-bound C3 deposits, including a monoclonal antibody to C3d (mAb 3d29) that does not recognize native C3 or C3b. To determine whether this antibody can be used to noninvasively monitor *Mycobacterium tuberculosis* (M. tb) infection, female C3HeB/FeJ mice were infected with aerosolized M. tb. 3d29 was covalently labeled with Iodine-125. Infected and non-infected control mice were then injected with the radiolabeled probe. Single-photon emission computed tomography (SPECT)/CT imaging at 24 and 48 hours post-radiotracer injection was performed. Results showed that [$^{125}$I]3d29 was detected by SPECT and co-registered with CT images in order to localize [$^{125}$I]3d29 in injected mice. Lung tissue from similar animals was also immunostained for 3d29 and macrophages. Strong signal was detected by SPECT imaging in the lungs and spleens of infected mice, consistent with the location of granulomas in the infected animals. Low level signal was seen in the spleens of uninfected mice and no signal was seen in the lungs of healthy mice Immunofluorescence microscopy revealed that 3d29 in the lungs of infected mice co-localized with aggregates of macrophages (detected with anti-CD68 antibodies and DPA-713-IRDye680LT). 3d29 was detected in the cytoplasm of macrophages, consistent with the location of internalized M. tb. 3d29 was also seen in alveolar epithelial cells, indicating that it detects M. tb. phagocytosed by other CD68-positive cells. In conclusion, the results demonstrated that radiolabeled 3d29 can be used to detect and localize areas of infection with M. tb. Infection with M. tb is one of the leading causes of mortality worldwide, and incomplete treatment has led to multidrug resistant-strains of the disease. The presently disclosed imaging method is useful to ensure the effective and complete treatment of infected patients and is useful for monitoring disease activity in a wide range of other infectious and autoimmune diseases.

Accordingly, in an aspect the presently disclosed subject matter provides a method for detecting and/or monitoring a *Mycobacterium tuberculosis* (*M. tuberculosis*) infection in a subject, the method comprising: (a) administering to a subject an effective amount of a monoclonal antibody or antibody derivative which binds to C3d in the subject, wherein the monoclonal antibody or antibody derivative is conjugated to an imaging tag; and (b) detecting a signal generated by the imaging tag to detect and/or monitor the location of the *M. tuberculosis* infection in the subject.

In another aspect, the presently disclosed subject matter provides for the use of a monoclonal antibody or antibody derivative which binds to C3d for detecting and/or monitoring a *M. tuberculosis* infection in a subject, wherein the antibody or antibody derivative is conjugated to an imaging tag.

In yet another aspect, the presently disclosed subject matter provides for the use of antibody 3d29 or a derivative thereof for detecting and/or monitoring a *M. tuberculosis* infection in a subject, wherein the antibody or antibody derivative is conjugated to an imaging tag.

In some embodiments, the antibody or antibody derivative comprises 3d29 or a derivative thereof. Suitable 3d29 antibodies and derivatives of 3d29 antibodies and their sequences can be found in international PCT application publication no. WO 2014/028865, which is incorporated herein by reference in its entirety. In some embodiments, the antibody or antibody derivative binds to infected tissue in the subject. In some embodiments, the infected tissue comprises inflamed tissue. In some embodiments, the infected tissue is selected from the group consisting of lung, spleen and any other extrapulmonary infected tissue. In some embodiments, the antibody or antibody derivative co-localizes with alveolar and peripheral phagocytes in *M. tuberculosis* infected lung sections in the subject and/or co-localizes with aggregates of macrophages in the lungs of infected subjects. In some embodiments, the imaging tag is a fluorescent tag and/or a radiolabel. In some embodiments, the imaging tag comprises any radioiodine nuclide. In some embodiments, the imaging tag comprises $^{125}$I, $^{123}$I, $^{124}$I, or $^{131}$I. In some embodiments, the imaging tag comprises LISSAMINE, IRDye608RD or IRDye800CW.

In some embodiments, the step of detecting the signal comprises performing an imaging method selected from the group consisting of computed tomography (CT), fluorescence imaging, and single-photon emission computed tomography (SPECT), positron emission tomography (PET), and combinations thereof. In some embodiments, the step of detecting the signal comprises performing SPECT/CT imaging. In some embodiments, the step of detecting the signal comprises performing PET/CT.

In some embodiments, the step of administering comprises injecting the antibody or antibody derivative into the subject. In some embodiments, injecting comprises intravenous or intraperitoneal injection.

In some embodiments, the method further comprises treating the subject for *M. tuberculosis* infection. In some embodiments, treating comprises administering to the subject an effective amount of an antibiotic agent, an anti-inflammatory agent, or a combination thereof.

As used herein, "anti-inflammatory agent" refers to an agent that may be used to prevent or reduce an inflammatory response or inflammation in a cell, tissue, organ, or subject. Exemplary anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules. The anti-inflammatory agent may be included in a pharmaceutical composition comprising the antibody or antibody derivative which binds C3d (e.g., 3d29 or a derivative thereof), optionally together with an antibiotic agent. In some embodiments, the anti-inflammatory agent is conjugated directly or indirectly to the antibody or antibody derivative (e.g., antibody or antibody derivative which binds to C3d, e.g., 3d29 or a derivative thereof), for example, to target the anti-inflammatory agent to the location of the *M. tuberculosis* infection and/or inflammation in the subject (e.g., infected and/or inflamed tissue, e.g., lungs and/or spleen).

Antibiotic agents include without limitation those that affect the bacterial cell wall, such as penicillins and cephalosporins, the cell membrane, such as polymyxins, interfere with essential bacterial enzymes, such as rifamycins, lipiarmycins, quinolones, and sulfonamides, target protein synthesis, such as macrolides, lincosamides and tetracyclines, cyclic lipopeptides, such as daptomycin, glycylcyclines, such as tigecycline, oxazolidinones, such as linezolid, lipiarmycins, such as fidaxomicin, fluoroquinolones, such as gemifloxacin, lipoglycopeptides, such as telavancin, and macrocyclics, such as fidaxomicin. Exemplary antibiotic agents include, without limitation, rifampicin, pyrazinamide, ethambutol, streptomycin, isoniazid, amoxicillin, ampicillin, bacampicillin, carbenicillin, cloxacillin, dicloxacillin, flucloxacillin, mezlocillin, nafcillin, oxacillin, penicillin G, penicillin V, piperacillin, pivampicillin, pivmecillinam, ticarcillin, cefacetrile (cephacetrile), cefadroxil (cefadroxyl), cefalexin (cephalexin), cefaloglycin (cephaloglycin), cefalonium (cephalonium), cefaclor, cefamandole, cefmetazole, cefcapene, cefdaloxime, aztreonam, imipenem, doripenem, meropenem, ertapenem, azithromycin, erythromycin, clarithromycin, dirithromycin, roxithromycin, ketolides, telithromycin, clindamycin, lincomycin, pristinamycin, amikacin, gentamicin, kanamycin, neomycin, flumequine, nalidixic acid, oxolinic acid, piromidic acid, ciprofloxacin, enoxacin, lomefloxacin, balofloxacin, gatifloxacin, grepafloxacin, levofloxacin, sulfamethizole, sulfamethoxazole, sulfisoxazole, demeclocycline, doxycycline, minocycline, oxytetracycline, tetracycline, chloramphenicol, metronidazole, tinidazole, nitrofurantoin, vancomycin, telavancin, linezolid, bacitracin, polymyxin B, and viomycin.

The antibiotic agent may be included in a pharmaceutical composition comprising the antibody or antibody derivative which binds C3d (e.g., 3d29 or a derivative thereof), optionally together with an anti-inflammatory agent. In some embodiments, the antibiotic agent is conjugated directly or indirectly to the antibody or antibody derivative (e.g., antibody or antibody derivative which binds to C3d, e.g., 3d29 or a derivative thereof), for example, to target the antibiotic agent to the location of the *M. tuberculosis* infection and/or inflammation in the subject (e.g., infected and/or inflamed tissue, e.g., lungs and/or spleen).

In some embodiments, the subject is human.

In another aspect, the presently disclosed subject matter provides a method of treating a *M. tuberculosis* infection in a subject in need thereof, the method comprising: (a) administering to a subject an effective amount of a monoclonal antibody or antibody derivative which binds to C3d, wherein the monoclonal antibody or antibody derivative is conjugated to an imaging tag, and wherein the antibody or antibody derivative binds to infected tissue in the subject; (b) detecting a signal generated by the imaging tag to detect and/or monitor the location of the *M. tuberculosis* infection in the subject; and (c) administering to the subject an effective amount of an antibiotic agent, an anti-inflammatory agent, or a combination thereof. In some embodiments, the infected tissue comprises inflamed tissue. In some embodiments, the antibiotic agent and/or anti-inflammatory agent are administered to the location of the *M. tuberculosis* infection in the subject. In some embodiments, the antibiotic agent and/or anti-inflammatory agent are administered to the location of the inflammation in the subject. In some embodiments, the subject is human.

"Sequence identity" or "identity" in the context of proteins or polypeptides refers to the amino acid residues in two amino acid sequences that are the same when aligned for maximum correspondence over a specified comparison window.

Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp (1989) *CABIOS* 5:151-153; Higgins et al. (1992) *Comput. Appl. Biosci.* 8:189-191) and found in the MegAlign™ program of the LASERGENE bioinformatics computing suite (DNASTAR Inc., Madison, Wis.).

It is well understood by one skilled in the art that many levels of sequence identity are useful in identifying proteins or polypeptides (e.g., from other species) wherein the proteins or polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present presently disclosed subject matter, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

The term "antibody," also known as an immunoglobulin (Ig), is a large Y-shaped protein produced by B cells that is used by the immune system to identify and neutralize foreign objects such as bacteria and viruses by recognizing a unique portion (epitope) of the foreign target, called an antigen. As used herein, the term "antibody" also includes an "antigen-binding portion" of an antibody (or simply "antibody portion"). The term "antigen-binding portion," as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); e.g., Bird et al. (1988) *Science* 242:423-426; Huston et al. (1988) *Proc. Natl. Acad Sci. USA* 85:5879-5883; and Osbourn et al. (1998) *Nature Biotechnology* 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. The terms "monoclonal antibodies" and "monoclonal antibody composition," as used herein, refer to a population of antibody polypeptides that contain only one species of antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities. Moreover, an isolated antibody may be substantially free of other cellular material and/or chemicals.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

More particularly, as described herein, the presently disclosed compositions can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. The presently disclosed compositions can also be administered intratumorally, such that the compositions are directly administered into a solid tumor, such as by injection or other means.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

As used herein, the term "reduce" or "inhibit," and grammatical derivations thereof, refers to the ability of an agent to block, partially block, interfere, decrease, reduce or deactivate a pathway or mechanism of action. Thus, one of ordinary skill in the art would appreciate that the term "reduce" encompasses a complete and/or partial loss of activity, e.g., a loss in activity by at least 10%, in some embodiments, a loss in activity by at least 20%, 30%, 50%, 75%, 95%, 98%, and up to and including 100%.

In another aspect, the presently disclosed subject matter provides a pharmaceutical composition alone or in combination with one or more additional therapeutic agents in admixture with a pharmaceutically acceptable excipient. In some embodiments, the pharmaceutical composition comprises an antibody or antibody derivative which binds to C3d in combination with an antibiotic agent, an anti-inflammatory agent, or both an antibiotic agent and anti-inflammatory agent, optionally with a pharmaceutically acceptable carrier, diluent, or excipient, for example, for detecting and/or diagnosing and/or monitoring a M. tuberculosis infection in a subject.

One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent.

Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) "Pharmaceutical Salts", *J. of Pharm. Sci.* 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams and Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

Reagents

Recombinant Human C3d:

Recombinant human C3d was used as an immunogen for antibody generation. It was also used as a target antigen in ELISA binding studies and Western blot analysis. C3d was generated using the pGEX expression system (GE Healthcare) in *E. coli* as previously described (Li et al., 2008). The C3d construct comprised amino acids 996-1303 of the precursor Pro-C3 protein. Briefly, ampicillin-resistant colonies were expanded to 1 liter in Luria-Bertani (LB) broth. The cultures were grown at 37° C. until an A600 of 0.3 was achieved. Cultures were induced with 0.3 mM isopropyl-β-D-thiogalactoside at 30° C. overnight before harvesting by centrifugation. Harvested pellets were resuspended in glutathione S-transferase column buffer (50 mM Tris-HCl, pH 8.0, 250 mM NaCl, 1 mM EDTA) and lysed by sonication. Lysate was clarified by centrifugation and applied to a GSTrap HP column (GE Biosciences). C3d was cleaved from the column by digesting with 50 units of thrombin overnight at 4° C. and subsequently purified by size-exclusion chromatography. The purity of C3d was verified using SDS-PAGE. A second form of recombinant human C3d encompassing the same region was also produced as previously described (Kulik et al., 2007). Binding of the antibodies to this construct by ELISA was performed to ensure that the antibodies bound a C3d epitope that was present on protein generated through independent methods.

Recombinant Murine C3d:

Murine C3d was cloned from murine cDNA using a forward primer containing a BamH I restriction site (5' CGC GGA TCC GCG GCT GTG GAC GGG GAG 3') and a reverse primer containing an EcoRI restriction site (5' CCG GAA TTC CGG TCA TCA ACG GCT GGG GAG GTG 3'). The amplified fragment was inserted into pGEX vector and generated by the same methods used for the human C3d. This recombinant murine C3d was used as a target antigen in ELISA binding studies.

Recombinant CR2 SCR1-2:

Recombinant maltose-binding protein-tagged (MBP-tagged) CR2 SCR1-2 (MBP-CR2) comprising residues 1-133 of wild-type CR2 and encompassing the first 2 SCR modules were expressed in *E. coli* as previously described (Szakonyi et al., 206; Young et al., 2007; Young et al., 2008). Briefly, MBP-CR2 SCR1-2-transformed colonies of *E. coli* BL21 were expanded to 4 liters in LB media and grown at 37° C. until an A600 of 0.3 was obtained. Cultures were then induced with 0.3 mM IPTG at 20° C. overnight before harvesting by centrifugation. Resulting cell pellets were resuspended in a column buffer containing 20 mM Tris-HCl (pH 7.4), 0.2 M NaCl, and 1 mM EDTA prior to lysis by sonication. The resulting lysate was clarified by centrifugation and recombinant MBP-CR2, which was initially purified by successive amylose-affinity and size-exclusion chromatographic steps. Finally, the recombinant MBP-CR2 was applied to a C3d-affinity column generated by binding GST-tagged C3d to a GSTrap column (GE Biosciences) and eluted with a linear NaCl gradient. The resulting protein was then concentrated, buffer-exchanged into PBS (1.6 mM MgCl2, 0.9 mM KCl, 0.5 mM KH2PO4, 45.6 mM NaCl, 2.7 mM Na2HPO4, pH 7.4), and its purity tested by SDS-PAGE.

Purified Complement Proteins:

Binding studies were also performed using commercially available purified complement proteins (C3, C3b, iC3b, and C3d; all from CompTech).

Mice and Animal Models

To generate monoclonal antibodies against C3d, mice with a targeted deletion of the C3 gene were immunized with recombinant human C3d. These mice were generated as previously described (Wessels et al., 1995). C57BL/6 wild-type mice were used for some in vivo experiments, and serum was collected from these mice for in vitro assays that required murine complement proteins. Mice with targeted deletion of the gene for factor H were generated as previously described (Pickering et al., 2002). Kidney sections from these mice were used to test binding of the anti-C3d antibodies to tissue-bound C3 fragments in vitro, and fH−/− mice were injected with purified anti-C3d antibodies to test binding of the antibodies to tissue-bound C3 fragments in vivo. Kidney sections from mice that have targeted deletion of the gene for factor I, and thus do not generate iC3b, were used to test whether the antibodies bind to the C3b fragment (Rose et al., 2008). Mice with targeted deletion of the gene for complement factor B gene were used as a negative control for binding of the FITC-labeled anti-C3d antibodies against CNV lesions (Matsumoto et al., 1997). To induce CNV lesions, 3-month-old mice were anesthetized (xylazine and ketamine, 20 and 80 mg/kg, respectively) and their pupils were dilated (2.5% phenylephrine HCl and 1% atropine sulfate). Argon laser photocoagulation (532 nm, 100 nm spot size, 0.1-second duration, 100 mW) was used to generate 4 laser spots in each eye surrounding the optic nerve, using a hand-held coverslip as a contact lens (Rohrer et al., 2009). For tail vein injections, the vein was vasodilated by heat, a 25-G needle was inserted, and a volume of 100 µl was injected. The dosing and treatment schedule is outlined in the Results section.

Immunization Protocol and Hybridoma Generation

The humoral immune response to the immunizations was assessed by ELISA using C3d as the target. The mice developed high titers of anti-C3d antibodies after 3 injections of 60 to 100 µg of protein (the first injection using complete Freund's adjuvant and the second and third injections using incomplete Freund's adjuvant). The mice were then injected intraperitoneally with 100 µg of C3d, and after 72 hours the spleen was harvested for fusion to Sp2/0 hybridoma cells (Kulik et al., 2009). To prevent exposure of the anti-C3d hybridomas to C3d during the cloning process, the cells were grown in serum-free media supplemented with hypoxanthine-aminopterin-thymidine (HAT) (Sigma-Aldrich), and peritoneal macrophages from C3−/− mice were used as the feeder cells during this process. Single-cell clones were generated and specificity of the clones to C3d was confirmed by ELISA, as described below.

ELISAs

C3d ELISAs:

To assess the reactivity of antibodies against C3d, ELISAs were performed using purified forms of C3 activation fragments from several different sources (see Reagents section above). Direct ELISAs were performed by affixing 30-50 µg of the C3 fragment to the ELISA plate overnight at 4° C. and pH 7.4. The plates were blocked with 1% BSA in PBS for 2 hours at room temperature. Antibody was added to the wells at 5 µg/ml, incubated, and the plates were washed 4 times. Bound antibodies were then detected with HRP-conjugated anti-mouse IgG (MP Biomedicals). Sandwich ELISAs were performed by incubating polyclonal anti-human C3d antibody (Dako) to the ELISA plates in order to capture the C3d. Binding of the antibodies to the captured C3d was then detected as above.

C3d-CR2/Anti-C3d Monoclonal Antibody Competition Assay:

Plates were incubated overnight at 4° C. with wild-type C3d at a concentration of 5 µg/ml in a 50 mM sodium bicarbonate buffer (pH 8.8). After coating, plates were blocked using 1% BSA in PBS (pH 7.4), for 1 hour at room temperature. Plates were then washed 3 times using PBS-Tween 20 (0.05%). Recombinant wild-type MBP-CR2 (10 µg/ml) was added to half of the C3d-coated wells to act as a positive control. To the other half of the C3d-coated wells, 10 µg/ml of recombinant wild-type MBP-CR2 containing 1 of the following anti-C3d monoclonal antibodies: 3d8B; 3d31; 3d15; 3d9a; 3d11; 3d16; 3d10; 3d3; or 3d29 at concentrations ranging from 1.625 to 26 µg/ml in PBS was added. After a 1-hour incubation period, the plates were washed and then incubated with commercially available HRP-conjugated anti-MBP antibody (New England Biolabs). After a further 1-hour incubation period, binding of MBP-CR2 to the plate-bound C3d was detected with 2,2'-azinobis(3-ethylbenzthiazoline-6-sulfonic acid) (ABTS).

Western Blot Analysis and Pull-Down Studies

Western blot analysis was performed by resolving 1 µg of purified complement protein on a 10% Bis-Tris polyacrylamide gel (Invitrogen) under denaturing conditions. The protein was then transferred to a nitrocellulose membrane. C3 fragments were then detected by incubating the membrane with 25 µg of each antibody (0.5 mg/ml) for 1 hour at room temperature, and bound antibody was detected with HRP-conjugated anti-mouse IgG Immunoprecipitation of complement fragments was performed by adding 100 µg of antibody to 75 µl of protein G sepharose (GE Healthcare) preblocked with 1% BSA for 1 hour. The antibodies were incubated with the protein G sepharose for 2 hours, excess antibody was removed by washing the sepharose with PBS, 150 µl of serum from RAG-1 knockout mice was added, and the mixture was incubated overnight at 4° C. The protein G sepharose was then washed 3 times in PBS, resuspended in loading buffer, and separated by SDS-PAGE. The isolated C3 fragments were detected by Western blot analysis using mAb 3d11.

Measurement of Antibody Affinities by Surface Plasmon Resonance

The binding of clones 3d8b, 3d9a, and 3d29 to recombinant human C3d was examined using a BIAcore 3000 (Biacore) at the University of Colorado Biophysics Core. C3d was immobilized on a carboxymethyl-dextran (CM5) chip using random amine coupling with 1-ethyl-3-[3-dimethylaminopropyl] carbodiimide hydrochloride/N-hydroxysulfosuccinimide as the activating reagent. Recombinant human C3d was immobilized at a concentration of 50 mg/ml in 100 mM sodium acetate, pH 5.0. The remaining activated groups on the surface of the chip were blocked with a 1-M ethanolamine solution (pH 8.5). Experiments were conducted in 10 mM HEPES, 150 mM NaCl, and 0.005% P20 (pH 7.4), and the chip was regenerated between runs with two 10-µl injections of 10 mM NaOH. Each antibody was injected at concentrations of 90, 30, and 10 nM for 1 minute at a flow rate of 50 µl per minute, and dissociation of the resulting antibody-C3d complexes was monitored for 10 minutes. All injections were performed in triplicate to verify reproducibility and all data were double referenced using a blank flow cell and a blank injection of buffer to account for nonspecific binding and baseline drift, respectively. Data were fit using a 1:1 Langmuir binding model and data analysis was performed using SCRUBBER-2 software (distributed by David Myszka of the University of Utah Center for Biomolecular Interactions).

Complement Assays

Zymosan Activation Assay:

Zymosan particles were opsonized with murine C3 fragments by incubating the particles with complement-sufficient mouse serum as previously described (Thurman et al., 2005). The particles were washed and then incubated with 2 µg of purified anti-C3d antibody, and bound antibody was detected with FITC-conjugated anti-mouse IgG (MP Biotech). The samples were analyzed by flow cytometry and compared with a positive control (C3 deposition detected with a polyclonal anti-mouse C3; MP Biomedicals) or with a negative control (no serum added). In some experiments, biotinylated antibodies were incubated with the particles in the presence of the activated serum, or fresh mouse serum was added to the particles at the incubation step. Bound antibody was then detected with streptavidin-FITC in order to test whether C3 and C3 fragments in the serum would compete with C3 on the zymosan surface for the antibody.

Alternative Pathway Hemolytic Assay:

This assay was performed as previously described (Thurman et al., 2005). Briefly, rabbit erythrocytes (Colorado Serum Company) were washed and then resuspended in a solution of 1.1% NaCl, 0.0025% Na-5,5 diethyl barbiturate (pH 7.35), 8 mM EGTA, and 2 mM MgCl2 (GVB/Mg/EGTA). Fifty microliters of this suspension was added to human serum (5-100 µl), and buffer solution was added to bring the final volume up to 150 µl. Erythrocytes in buffer without serum were used as a negative control, and erythrocytes added to 100 µl of distilled water were used as a positive control (complete lysis). Samples were incubated at 37° C. for 30 minutes, with occasional shaking to keep the cells in suspension. The reactions were stopped by adding 1.5 ml of cold PBS and the samples were spun at 1,000 g for 5 minutes. The optical density of each supernatant was read at 415 nm using a spectrophotometer (Bio-Rad). The concentration of serum that caused approximately 50% lysis of the erythrocytes was determined. The reactions were then repeated with the addition of 0 to 40 µg of each antibody. The percent lysis for each reaction was compared with serum alone, and the change in lysis was reported as a percentage.

Buffers:

DGVB2+ buffer: 1 mM MgCl2, 0.15 mM CaCl2, 71 mM NaCl, 0.1% (w/v) gelatin, 2.5% (w/v) dextrose, and 2.47 mM sodium 5',5"-diethyl barbiturate (pH 7.35); Mg2+ EGTA buffer: 10 mM Na2EGTA, 7 mM MgCl2, 59 mM NaCl, 0.083% (w/v) gelatin, 2.075% (w/v) dextrose, and 2.05 mM sodium 5',5"-diethyl barbiturate (pH 7.3-7.6); 10 mM EDTA buffer: 10 mM Na2EDTA, 128 mM NaCl, 0.1% (w/v) gelatin, and 4.45 mM sodium 5',5"-diethyl barbiturate (pH 7.35); 40 mM EDTA buffer: 40 mM Na2EDTA, 85 mM NaCl, 0.1% (w/v) gelatin, and 2.96 mM sodium 5',5"-diethyl barbiturate (pH 7.35).

Preparation of Cell-Bound C3b:

Ab-sensitized sheep erythrocytes (EA cells, 5 ml, 5×108/ml) obtained from CompTech were washed twice and resuspended in 5 ml of DGVB2+ buffer, mixed with 37.5 µg of human C1 in 5 ml of DGVB2+, and incubated for 15 minutes at 30° C. The resulting cells (EAC1) were washed twice and resuspended in 5 ml of DGVB2+, mixed with 50 µg of human C4 suspended in 5 ml of DGVB2+, and incubated for 15 minutes at 30° C. These cells (EAC1, 4) were washed twice and suspended in 5 ml of DGVB2+, mixed with 250 µg of human C3 and 5 µg of human C2 suspended in 5 ml of DGVB2+, and incubated for 30 minutes at 30° C. The resulting cells (EAC1, 4, 2, 3) were washed and resuspended in 5 ml of 10 mM EDTA buffer and incubated at 37° C. for 2 hours to allow for dissociation of the active classical pathway convertases. The resulting C3b-coated cells were washed twice in 5 ml 10 mM EDTA buffer, twice in 5 ml of 10 mM Mg2+ EGTA buffer, and resuspended in 10 mM Mg2+ EGTA buffer to a final concentration of 1×108 per milliliter. They were stored at 4° C. and used within 1 week.

Effects of Anti-C3 mAbs on the Activity of Cell-Bound C3bBbP Complexes:

C3b-coated sheep erythrocytes were prepared as described (Hourcade et al., 1995; Whaley et al., 1985). C3b-coated sheep erythrocytes (100 µl), 50 µl of purified factor D (5 ng in Mg2+ EGTA buffer), 50 µl of properdin (45 µg in Mg2+ EGTA buffer), and 50 µl of factor B (3-5 µg in Mg2+ EGTA buffer) were mixed together and incubated at 30° C. for 30 minutes. In some cases, the factor B was replaced by 50 µl of Mg2+ EGTA buffer. Samples were chilled to 4° C. and treated with 150 µl 40 mM EDTA buffer (40 mM Na2EDTA, 85 mM NaCl, 0.1% [w/v] gelatin, and 2.96 mM sodium 5',5"-diethyl barbiturate, pH 7.35), containing in some cases 1 µg of mouse anti-human C3d mAb. Samples were then incubated for 0 to 3 hours at 30° C. to permit spontaneous C3bBbP dissociation. In some cases, this incubation was undertaken with or without 400 µg of factor H for 30 minutes to assess factor H-dependent convertase decay acceleration. Functional convertases were then quantified by adding 150 µl of a 1:20 dilution of guinea pig serum (Colorado Serum) in 40 mM EDTA buffer to all samples, followed by incubation at 37° C. for 60 minutes. Additional samples included cell lysis controls in which cells were treated with 450 µl of distilled water alone and a negative control in which cells were treated with 450 µl of DGVB2+ buffer alone. All samples were then centrifuged and the OD414 of the supernatants was determined. Hemolytic activity levels were expressed as Z values, the average number of lytic sites or MAC pores formed per red blood cell, and were calculated using the expression: $Z=-\ln(1-y)$, where y is the proportion of lysed cells. Each determination was the average of duplicate points. All complement proteins were of human origin and were purchased from CompTech.

Immunofluorescence Microscopy

For immunofluorescence microscopy, sagittal sections of the kidneys were snap-frozen in OCT compound (Sakura Finetek USA). Five-micrometer sections were cut with a cryostat and stored at −80° C. until used. The slides were later fixed with acetone and stained with antibody against mouse C3 or mouse IgG. The slides were then counterstained with hematoxylin (Vector Laboratories) and viewed using an Olympus BX51 microscope. The anti-C3d antibodies were used at a concentration of 2 µg/ml for tissue staining. For immunofluorescence microscopy of RPE/choroid, flat-mount preparations were incubated with FITC-labeled antibodies. In brief, eyes were collected and immersion fixed in 4% paraformaldehyde for 30 minutes at 4° C. after which the anterior chamber, lens, and retina were removed. The eyecups were incubated in blocking solution (3% BSA, 10% normal goat serum, and 0.4% Triton-X in tris-buffered saline) for 1 hour followed by anti-C3d antibodies (1:100 of 1 mg/ml solution) overnight at 4° C. in blocking solution. Following extensive washing, eyecups were flattened using 4 relaxing cuts, coverslips were applied with Fluoromount (Southern Biotechnology Associates), and slides were examined by confocal microscopy (Leica TCS SP2 AOBS; Leica).

Fundus Imaging

Fundus imaging was performed using the Micron III retinal imaging microscope (Phoenix Research Laboratories), which is based on a custom optical system with a 300-W xenon light source and a 3-chip CCD camera, operating at 30 frames per second in linear/diagnostic mode. For imaging, mice were anesthetized, their pupils were dilated as described above and secured in the imaging cradle. Optical contact between the cornea of the mouse and the lens of the optical system was established through a drop of methylcellulose. A fundus photograph was obtained using bright-field imaging to focus on the CNV lesions, after which the mode was switched to FITC fluorescence imaging (excitation at 490 nm). JPEG images were exported to Adobe Photoshop to assemble the photos and to extract images of individual lesions. Images obtained with this system have a resolution element of approximately 4 μm. To improve visualization of individual lesions, contrast enhancement using identical parameters for control and experimental images was applied.

Statistics

Data were analyzed using GraphPad Prism software (GraphPad) and the results for groups are presented as the mean±SEM. Comparison between groups was performed using unpaired 2-tailed t tests. A P value of less than 0.05 was considered significant.

Study Approval

The mice were housed and maintained in the University of Colorado Center for Laboratory Animal Care in accordance with the NIH Guidelines for the Care and Use of Laboratory Animals. The CNV model procedures and fundus imaging were performed in accordance with the ARVO Statement for the Use of Animals in Ophthalmic and Vision Research and were approved by the IACUC of the Medical University of South Carolina. All other animal experiments and procedures were approved by the IACUC of the University of Colorado.

FIG. 11 Methods

Aerosol-infect C3HeB/FeJ (granulomatous TB) with live M. tb and wait ~8 weeks before imaging. Uninfected and infected mice were injected with ~3 mCi of [$^{125}$I]3d29 for SPECT-CT scans including an infected an uninfected mouse injected with 3 mCi each of [$^{125}$I]isotype control for a specific binding study. Uptake times included 24 and 48 h post-injection and were optimized at 24 hours post-injection for granuloma visualization. Infected mice were also subjected to ex vivo bisdistribution studies by injecting ~7 Ci of [125I]3d29 or [125I]isotype followed by a 24 hour uptake. All major tissues were collected to measure the % injected dose/gram of tissue. Lung sections were probed in vitro with 3d29-LISSAMINE or isotype-LISSAMINE conjugates and co-stained with anti-CD68 and anti-TSPO antibody to localize the cellular distribution of 3d29 in this mouse model of pulmonary TB.

Example 2

Development of Murine mAbs Against Recombinant Human C3 d

During complement activation, C3 undergoes a conformational change that exposes a reactive thioester bond (Serkova et al., 2010; Janssen et al., 2006). The thioester domain (TED) of C3 rotates during the conversion of C3 into C3b, altering the orientation of the TED on the surface of the molecule (Janssen et al., 2006). Domains within this region of C3b become increasingly exposed during the subsequent cleavages that generate iC3b, C3dg, and finally C3d (FIG. 1). In order to generate mAbs against epitopes on this region of C3, recombinant human C3d was produced using an *E. coli* expression system (Shaw et al., 2010) and immunized mice bearing a targeted deletion of the C3 gene (C3−/− mice) (Wessels et al., 1995). Although C3−/− mice have impaired humoral immunity (Wessels et al., 1995), immunization of these mice has previously been used to generate antibodies against human C3 (Li et al., 2007). It was found that C3−/− mice immunized with recombinant C3d immunogen in adjuvant developed a strong humoral response to C3d (data not shown).

Two fusions were performed using splenocytes of mice with high antibody titers against C3d, but both fusions failed to yield any reactive clones. Because the desired hybridomas would produce monoclonal antibodies specific to C3d, it was hypothesized that the failure to generate any clones was because C3 fragments generated by serum in the tissue culture media or from macrophages used in the cloning process bound to the B cell receptors of the reactive cells. This could potentially lead to apoptosis of the cells or interfere with the screening ELISA assay. Therefore, a third fusion was performed in which hybridomas were grown in serum-free media formulations. Because macrophages also have the capacity to synthesize all of the proteins of the alternative complement pathway and generate C3 fragments (Strunk et al., 1983), the feeder cells used during cloning were obtained by peritoneal lavage of C3−/− mice. Single-cell clones were generated and screened against C3d by ELISA, and 9 hybridomas producing monoclonal antibodies with strong ELISA reactivity against human C3d were identified (FIG. 2A). This ELISA was repeated multiple times during the cloning and purification process, and a representative experiment is shown.

To confirm that the monoclonal antibodies reacted with C3d and not with a contaminant in the immunogen, the antibodies were tested against C3d using a sandwich ELISA in which recombinant C3d was captured with a polyclonal anti-C3d capture antibody. To test the reactivity of the clones against murine C3d (which has 84% sequence identity with human C3d), indirect and sandwich ELISAs using recombinant murine C3d were performed. Direct ELISAs were also performed to test binding of the antibodies to recombinant human C3d from a second construct as well as to commercially available purified human C3d, and to recombinant cynomolgus C3d. The 9 clones all showed strong reactivity against each of these targets (data not shown). To test the antibodies for cross-reactivity against other plasma proteins, the C3d ELISA was repeated in the presence of wild-type and C3−/− mouse serum (FIG. 3). Serum was added across a range of dilutions (1:5 to 1:6,400), and no effect on the binding of the antibodies to C3d was observed.

Example 3

Specificity of mAbs 3d8b, 3d9a, and 3d29 to C3 Activation Fragments

Western blot analysis of human C3 and C3d was performed following separation of C3d and C3 fragments by SDS-PAGE, and the blots were probed with the 9 anti-C3d clones. Although one might expect epitopes recognized in SDS-denatured C3d to also be exposed on the intact C3 α chain in its denatured form, the antibodies demonstrated differential recognition of C3 and C3d in this assay (FIG. 2B). The antibodies displayed 3 distinct binding patterns by Western blot analysis: strong binding to C3d without substantial binding to C3 (Group 1); strong binding to the C3 α chain and C3d (Group 2); or weak binding to both proteins (Group 3). A commercially available polyclonal antibody against mouse C3 (MP Biomedicals; product 55557) bound fragments that approximate the sizes of the a and 13 chains of C3 and is shown on the right-most blot for comparison. The lower molecular weight bands may represent contaminants or degraded C3. Antibodies from each group displayed nearly identical patterns when run side by side (data not shown). Clone 3d11 recognized all of the C3 α chain fragments by Western blot analysis (FIG. 2C). To evaluate the binding of the antibodies to the different C3 fragments in their native form, immunoprecipitation reactions were performed using activated murine serum that contained a mixture of the various C3 fragments (FIG. 2D). The immunoprecipitated proteins were then detected by Western blot analysis with mAb 3d11. Antibodies 3d8b and 3d29 (Group 1) pulled down murine iC3b, C3dg, and C3d fragments; 3d11 (Group 2) did not pull down any murine C3 fragments; and 3d16 (Group 3) pulled down iC3b and C3dg fragments. The affinities of mAbs 3d8b, 3d9a, and 3d29 for human C3d were tested by surface plasmon resonance (FIG. 4). The measured affinities were: 3d8b: KD=0.47 nM; 3d9a: KD=0.37 nM; and 3d29: KD=1.06 nM.

Example 4

Effects of Anti-C3d mAbs on Surface-Bound C3 Convertase Activity

The alternative pathway C3 convertase is composed of C3b in complex with the factor B fragment Bb and the fluid-phase protein properdin (P). While C3bBbP dissociation occurs spontaneously (T½~5-10 minutes), this process is greatly accelerated by the fluid-phase complement regulator factor H. This latter reaction plays a critical role in protecting cells and tissues from complement-mediated damage and in preserving C3 homeostasis. Certain anti-C3 autoantibodies, referred to as C3 nephritic factors (C3Nef), stabilize the alternative pathway C3 convertase and confer to it resistance to factor H, thus permitting uncontrolled complement activation (Daha et al., 1976). To assess whether the anti-C3d antibodies have C3Nef-like activity, human C3bBbP complexes preassembled on sheep erythrocytes were first incubated with the anti-C3d antibodies or with buffer alone for various durations. The hemolytic activity of the remaining convertases was then quantified (FIG. 5A). The Group 1 mAbs (3d8b, 3d9a, and 3d29) did not have any effect on erythrocyte lysis, nor did the Group 2 clone 3d31. The loss of hemolytic activity due to spontaneous convertase dissociation during the incubation period in these samples was comparable to that of the control cells. In contrast, the Group 3 clones (3d3, 3d15, and 3d16) stabilized the convertase, causing greater erythrocyte lysis immediately (FIG. 5A), and after a 2-hour incubation period (FIG. 5B). In all cases, hemolysis was absolutely dependent on the presence of factor B in the preassembly step (FIGS. 5, C and D), thus confirming that the alternative pathway C3 convertase mediated the Group 3 effects. EGTA was included as a calcium chelator, thus precluding the involvement of the other complement activation pathways in the process. The impact of the anti-C3d antibodies on factor H activity was also examined. Factor H is an alternative pathway regulatory protein that limits alternative pathway activation by accelerating the decay of C3 convertase (Weiler et al., 1976) or by serving as a cofactor for factor I-mediated cleavage (inactivation) of C3b (Pangburn et al., 1977). The addition of factor H inhibited lysis of the erythrocytes in reactions containing each of the anti-C3d antibodies, indicating that none of the antibodies blocked the factor H binding site on the surface of C3b (FIG. 5E). This is consistent with recent data indicating that the binding site on C3b for the amino-terminal 4 short consensus repeats (SCRs) of factor H (CFH1-4), which harbor the factor I cofactor and C3bBb decay acceleration activities of factor H, lies outside the TED domain (which approximates to the C3d cleavage product) (Wu et al., 2009). Finally, the antibodies were tested in an alternative pathway hemolysis assay using normal human serum and rabbit erythrocytes. This is a standard assay for measuring alternative pathway activity on activator surfaces. Even when clones 3d8b, 3d9a, and 3d29 were added to the reaction mix at high concentrations, they did not increase erythrocyte lysis (data not shown).

Example 5

Effect of Anti-C3d mAbs on Binding of C3d by CR2

C3d is a ligand for CR2, which is expressed on B cells and follicular dendritic cells. Recognition of C3d by CR2 on B cells lowers the threshold for B cell activation by the B cell receptor (Lyubchenko et al., 2005). CR2 also binds to the iC3b, C3dg, and C3d fragments of C3, similar to the Group 1 monoclonal antibodies. Consequently, signaling by CR2 is important in the development of the humoral immune response and autoimmunity (Dempsey et al., 1996). It was tested whether the mAbs against C3d block this interaction (FIG. 6A). Using an in vitro CR2-C3d binding assay, it was found that clones 3d8b, 3d9a, 3d11, 3d29, and 3d31 blocked CR2 from binding C3d, whereas the other antibodies did not. Dose response curves for the Group 1 antibodies demonstrated nearly complete inhibition of CR2 binding by 3d8b (FIG. 6B). Clones 3d9a and 3d29 achieved approximately 80% inhibition of binding by CR2 when added at high concentrations (FIG. 6C and FIG. 6D). The inability of 3d10 to block CR2 binding at any of the concentrations tested is shown in FIG. 6E. These results raise the possibility that mAbs 3d8b, 3d9a, 3d11, 3d29, and 3d31 may have immunomodulatory function.

Example 6

Binding of Anti-C3d mAbs to Surface-Bound C3 Activation Fragments In Vitro

To assess the ability of the mAbs to bind native C3 fragments bound to activating surfaces, zymosan particles were opsonized with C3 fragments by incubation with mouse serum (Thurman et al., 2005). The particles were then incubated with the antibodies, and bound antibodies were detected by flow cytometry (FIG. 7A). mAbs 3d8b, 3d9a, and 3d29 bound to the opsonized zymosan particles, whereas the other mAbs did not. To test whether intact C3 or C3 activation fragments in serum could compete with the C3 fragments on the zymosan surface, this assay was repeated and the particles were incubated with antibody in the presence of activated or fresh serum (FIGS. 7, B and C). The addition of serum to the reactions did not reduce binding of the antibody to the particles. To test the binding of these antibodies to C3 deposits in tissues, sections were made from the kidneys of factor H-deficient (fH−/−) mice. The glomeruli of these mice are characterized by glomerulonephritis and have abundant deposits of the C3 activation fragments iC3b and C3dg/C3d (28, 29). Clones 3d8b, 3d9a, and 3d29 bound to sites in the acetone-fixed sections in a pattern indistinguishable from that obtained using a polyclonal antibody against C3 (FIG. 8A and FIG. 8B). 3d8b, 3d9a, and 3d29 did not bind to the glomeruli of factor I-deficient mice (FIG. 8B; results not shown for 3d8b and 3d9a), confirming that the antibodies are specific to downstream cleavage fragments (iC3b, C3dg, and C3 d).

Example 7

In Vivo Targeting of Anti-C3d mAbs to Tissue Sites of Complement Activation

Next, it was sought to determine whether the antibodies would bind to tissue-bound C3 fragments when injected in vivo. The antibodies were injected intravenously into fH−/− mice, which do not have glomerular deposits of endogenous IgG (29). After 24 hours, the kidneys were harvested and immunostained for IgG (FIG. 9A). mAbs 3d8b, 3d9a, and 3d29 were readily detected along the glomerular basement membrane in a pattern indistinguishable from that of the C3 fragments, demonstrating that they bound to C3 deposits in the glomerular capillary wall after intravenous injection. To confirm that endogenous deposits of IgG were not being detected, mAb 3d29 was biotinylated and injected into fH−/− mice. Glomerular binding of the antibody was detected using streptavidin-FITC (FIG. 9A). C3 fragments are ordinarily deposited along the tubular basement membrane of wild-type mice (Thurman et al., 2003). Tubular C3 deposits are not seen in fH−/− mice, likely because most C3 is consumed in the fluid phase in these mice (Pickering et al., 2002; Renner et al., 2011). No IgG was detected along the tubular basement membrane of fH−/− mice injected with the anti-C3d antibodies. However, when biotinylated 3d29 was injected into wild-type mice, it was detected along the tubular basement membrane and colocalized with the C3 deposits (FIG. 9B). These results indicate that mAbs 3d8b, 3d9a, and 3d29 target and bind to tissue deposits of C3 activation fragments in the glomeruli of nephritic mice and in the tubulointerstitium of unmanipulated wild-type mice.

Example 8

In Vivo Imaging of Anti-C3d mAbs Targeted to Ocular Sites of Complement Activation To test whether the targeted antibodies could be visualized in vivo, a system amenable to optical imaging, the eye, was employed. Complement activation is involved in the pathology of age-related macular degeneration (AMD). Complement components, including C3 (Hageman et al., 2001), anaphlatoxins C3a and C5a (Nozaki et al., 2006), as well as components of the membrane attack complex (MAC) (Hageman et al., 2001) have been identified within pathological structures in AMD (e.g., drusen, Bruch's membrane), and single nucleotide polymorphisms in complement genes are risk factors for AMD (Leveziel et al., 2011). AMD results in vision loss from either atrophy of the retinal pigmented epithelium (RPE) followed by loss of photoreceptors, or choroidal neovascularization (CNV) followed by loss of photoreceptors. The latter process can be mimicked in mice by damaging the blood-retina barrier using laser photocoagulation, which triggers ingrowth of choroidal blood vessels into the subretinal space in a complement-dependent fashion (Rohrer et al., 2009). Likewise, complement deposition has been shown to occur at the site of injury (Rohrer et al., 2009; Nozaki et al., 2006). Using the systemic CR2 targeting strategy, it was shown that complement inhibition delivered in this fashion (CR2-fH) can ameliorate CNV (Rohrer et al., 2009; Rohrer et al., 2012). It was evaluated whether complement activation in the RPE/choroid of laser-damaged mice using the anti-C3d mAbs could be directly imaged. First, the antibodies were tested to determine which of them recognize C3d epitopes in the CNV lesion sites in flat-mounted RPE/choroid. Since fluorescently labeled antibodies are required for in vivo imaging, only FITC-labeled antibodies were tested. Of the FITC-labeled mAbs, clone 3d29 demonstrated the best binding to the CNV lesion in lightly fixed tissues (4% paraformaldehyde for 30 minutes) (FIG. 10A). An isotype control antibody (HB5) was also tested in order to confirm the specificity of binding by 3d29 (FIG. 10B). Since complement factor B knockout mice (fB−/−) show no increase in C3 in the RPE/choroid in response to the lesion and fail to develop significant CNV (11), fB−/− mice were used as negative controls for FITC-labeled mAb binding (FIG. 10C). For in vivo imaging, CNV lesions were generated and 200 μg (200 μl of antibody at a concentration of 1 mg/ml) of FITC-labeled 3d29 or HB5 was injected intravenously on day 3 after CNV induction, a time point previously shown to correspond to the peak of C3 deposition within the lesion (Rohrer et al., 2009). Fundus imaging of the animals 6, 24, and 48 hours after the injection was used. The CNV lesions are readily apparent in bright-field images as depigmented areas (FIGS. 10, D and F). At the 6-hour time point, unbound FITC-labeled antibody was still visible in the retinal and choroidal vasculature, obscuring positive staining. Twenty-four hours after antibody injection, a strong fluorescent signal was detected in the CNV lesions of 3d29-injected mice (FIG. 10G). Little signal was detected in the lesions of HB5-injected mice (FIG. 10E). At 48 hours, while the positive signal for 3d29-injected mice was still present, the intensity was less pronounced. These results indicate that 3d29 is retained in RPE/choroidal tissue deposits of C3 activation fragments at the posterior pole of CNV-lesioned mice at a high enough concentration that it can be visualized in the living eye using conventional imaging techniques.

Example 9

Discussion

This report describes the development of 3 mAbs (the Group 1 antibodies 3d8b, 3d9a, and 3d29) against the C3 activation fragment C3d that do not bind to intact C3 in its native conformation. These 3 antibodies recognize an epitope on iC3b, C3dg, and C3d that is either generated or exposed during complement activation. This epitope is probably closely related to the CR2 binding site that is buried within the native C3 structure (van den Elsen et al., 2011). To successfully create these antibodies, several modifications were made to standard methods of hybridoma fusion: the hybridoma cells were grown under serum-free conditions, and macrophages from C3−/− mice were used as feeder cells during the cloning process. This approach allowed the generation of 9 mAbs against human C3d that also reacted with murine and cynomolgus C3d.

mAbs 3d8b, 3d9a, and 3d29 demonstrated strong binding to SDS-denatured C3d by Western blot analysis, but no detectable binding to SDS-denatured C3 or C3b (FIG. 2B). The same mAbs specifically pulled down iC3b, C3dg, and C3d from a mixture that also contained intact C3 and C3b (FIG. 2D). These 3 mAbs also bound to C3 fragments on the surface of opsonized zymosan particles in vitro (FIG. 7A), demonstrating the ability to bind sur-face-bound C3 fragments. Certain anti-C3 antibodies are known to stabilize C3 convertases, effectively amplifying complement activation. The 3 clones that target tissue-bound C3 fragments did not show any activating activity with the use of several different in vitro assays (FIG. 5). Based on their ability to compete for CR2 binding to C3d (FIG. 6), an overlapping or closely associated binding site is assumed. The Group 3 antibodies (3d3, 3d15, and 3d16) stabilized C3 convertases that were preassembled on sheep red blood cells (FIG. 5). None of the antibodies described here prevented factor H-mediated dissociation of the C3 convertase. When mice with glomerulonephritis were injected with mAbs 3d8b, 3d9a, or 3d29, the antibodies accumulated at the site of C3 fragment deposits within the glomeruli, demonstrating that the antibodies can be used to target tissue-bound iC3b and C3d at this location (FIG. 9A). When injected into wild-type mice, these antibodies bound to C3 fragments deposited along the tubular basement membrane (which have deposition of C3 fragments at baseline; FIG. 9B). Because C3 fragments are present in the plasma of fH−/− mice, and wild-type mice have high circulating levels of intact C3, these experiments verified that mAbs 3d8b, 3d9a, and 3d29 preferentially bind to the tissue-bound iC3b and C3d activation fragments, even in the presence of circulating C3 and C3 fragments.

A major obstacle to the development of a high-affinity targeting protein for C3 activation fragments is that the protein must distinguish the cleavage fragments from intact C3. The high affinity of these antibodies for C3d and the ability to deliver agents to sites of C3d deposition in vivo, make them invaluable tools for the development of diagnostic and therapeutic agents. The ability to block the C3d-CR2 interaction further raises the possibility that these antibodies will have immunomodulatory effects. In addition, when used for tissue analysis ex vivo, these antibodies can also be used to specifically detect deposits of iC3b, C3dg, and C3d fragments in tissues (FIG. 8). These antibodies cross-react with murine, human, and cynomolgus C3d, making them suitable for both preclinical and clinical studies. 41 commercially available mAbs against cleavage fragments of human C3 have been identified (not including antibodies against C3a), 11 of which are described by the vendors as reacting with iC3b and/or C3d. None of the available antibodies had been tested for species cross-reactivity, CR2 inhibition, or in vivo targeting, and only 1 of the antibodies is reported as functional in ELISAs, Western blot analysis, flow cytometry, and immunohistochemistry (Quidel antibody A209). Unlike the antibodies described (FIG. 5), however, that antibody stabilized the C3 convertase on sheep erythrocytes (data not shown). Similarly, 3 other commercial antibodies specific to epitopes in C3d have been tested in this assay and were all found to stabilize the C3 convertase (Dennis Hourcade, unpublished observations). Thus, although a wide range of antibodies against human C3 are available, based on data available from the vendors and based on our own experiments, none of the commercial antibodies against iC3b or C3d are comparable to mAbs 3d8b, 3d9a, or 3 d29.

The detection of glomerular C3 deposition is critical for the accurate diagnosis of glomerulonephritis, and renal biopsy tissue is routinely stained for C3 fragments. The antibodies and methods described herein may advance our ability to detect and monitor tissue C3 deposition. An MRI-based method for the noninvasive detection of glomerular C3 has been developed, and these high-affinity antibodies may improve the sensitivity of this method. In the current study, it has been demonstrated that FITC-labeled 3d29 was visualized in live animals using conventional fluorescence imaging. This enabled noninvasive detection of C3d deposits within the RPE/choroid of mice with CNV. Finally, targeted complement inhibitors have also demonstrated great promise for the treatment of inflammatory diseases (Atkinson et al., 2005; Sekine et al., 2011; Song et al., 2003). These antibodies may provide a high-affinity targeting vector for the delivery of novel therapeutic agents to sites of tissue inflammation.

The exact epitope of these antibodies has not yet been identified. The antibodies were screened against a panel of C3d mutants, but identification of the exact epitope on C3d was not successful (data not shown). This suggests that the antibodies may recognize a complex epitope not evaluated by that assay. Epitope mapping studies of these antibodies are underway. However, subtle differences between the antibodies, such as the superior ability of 3d8b to block CR2 binding compared with that of 3d9a and 3d29, suggest that they recognize distinct epitopes. Identification of the binding site for each antibody may help predict biologic functions of the antibodies, as one may then predict interactions of the C3 molecules that will be interrupted by the antibodies.

Autoimmune diseases are frequently life long and are characterized by flares and remissions. The immunomodulatory drugs used to treat these diseases are effective, but can cause serious side effects. Thus, as with cancer, the treatment of autoimmune diseases hinges upon the accurate assessment of disease activity. Unfortunately, current molecular imaging methods for detecting tissue inflammation, such as white blood cell scans, lack the senbodies sitivity and specificity necessary for monitoring autoimmune disease activity (Sargsyan et al., 2012). Because C3 fragments are abundant and durable markers of inflammation, they represent a powerful biomarker of tissue inflammation. Quantitative methods of detecting tissue C3 fragment deposits would improve our ability to monitor a patient's disease activity and response to therapy and would advance the application of "personalized medicine" to the autoimmune diseases. Our studies demonstrate that mAbs 3d8b, 3d9a, and 3d29 can be employed as molecular imaging probes for the detection of complement activation.

In conclusion, mAbs against C3 activation fragments have been successfully generated. Three of the antibodies recognize breakdown products of C3 (iC3b, C3dg, and C3d) but do not bind to intact C3 in its native state. It has been demonstrated that these antibodies target tissue-bound C3 fragments in vivo, despite high circulating levels of intact C3. Antibodies specific to tissue-bound C3 activation fragments may be employed for targeted delivery of therapeutic and diagnostic agents to sites of tissue inflammation. Radiologic methods of detecting these antibodies could provide an important new tool for detecting and monitoring tissue inflammation. It has been demonstrated that fluorescently labeled antibody was detected in live animals with CNV. Now that therapeutic complement inhibitors have been approved for clinical use (Rother et al., 2007), noninvasive methods of detecting complement activation within tissues will be increasingly important in therapeutic decision making.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

Ricklin D, Hajishengallis G, Yang K, Lambris J D. Complement: a key system for immune surveillance and homeostasis. *Nat Immunol.* 2010; 11(9):785-797.

Walport M J. Complement. Second of two parts. *N Engl J Med.* 2001; 344:1140-1144.

Law S K, Dodds A W. The internal thioester and the covalent binding properties of the complement proteins C3 and C4. *Protein Sci.* 1997; 6(2):263-274.

Sahu A, Kozel T R, Pangburn M K. Specificity of the thioester-containing reactive site of human C3 and its significance to complement activation. *Biochem J.* 1994; 2:429-436.

Sahu A, Pangburn M K. Covalent attachment of human complement C3 to IgG. Identification of the amino acid residue involved in ester linkage formation. *J Biol Chem.* 1994; 269(46):28997-29002.

Schulze M, Pruchno C J, Burns M, Baker P J, Johnson R J, Couser W G. Glomerular C3c localization indicates ongoing immune deposit formation and complement activation in experimental glomerulonephritis. *Am J Pathol.* 1993; 142(1):179-187.

Hageman G S, Luthert P J, Victor Chong N H, Johnson L V, Anderson D H, Mullins R F. An integrated hypothesis that considers drusen as biomarkers of immunemediated processes at the RPE-Bruch's membrane interface in aging and age-related macular degeneration. *Prog Retin Eye Res.* 2001; 20(6):705-732.

Atkinson C, et al. Targeted complement inhibition by C3d recognition ameliorates tissue injury without apparent increase in susceptibility to infection. *J Clin Invest.* 2005; 115(9):2444-2453.

Serkova N J, et al. Renal inflammation: targeted iron oxide nanoparticles for molecular MR imaging in mice. *Radiology.* 2010; 255(2):517-526.

Sargsyan S A, et al. Detection of glomerular complement C3 fragments by magnetic resonance imaging in murine lupus nephritis. *Kidney Int.* 2012; 81(2):152-159.

Rohrer B, et al. A targeted inhibitor of the alternative complement pathway reduces angiogenesis in a mouse model of age-related macular degeneration. *Invest Ophthalmol Vis Sci.* 2009; 50(7):3056-3064.

Rohrer B, Coughlin B, Bandyopadhyay M, Holers V M. Systemic human CR2-targeted complement alternative pathway inhibitor ameliorates mouse laser-induced choroidal neovascularization. *J Ocul Pharmacol Ther.* 2012; 28(4):402-409.

Webb S. Pharma interest surges in antibody drug conjugates. *Nat Biotechnol.* 2011; 29(4):297-298.

Guthridge J M, et al. Structural studies in solution of the recombinant N-terminal pair of short consensus/complement repeat domains of complement receptor type 2 (CR2/CD21) and interactions with its ligand C3dg. *Biochemistry.* 2001; 40(20):5931-5941.

Isenman D E, Leung E, Mackay J D, Bagby S, van den Elsen J M. Mutational analyses reveal that the staphylococcal immune evasion molecule Sbi and complement receptor 2 (CR2) share overlapping contact residues on C3d: implications for the controversy regarding the CR2/C3d cocrystal structure. *J Immunol.* 2010; 184(4):1946-1955.

Dempsey P W, Allison M E, Akkaraju S, Goodnow C C, Fearon D T. C3d of complement as a molecular adjuvant: bridging innate and acquired immunity. *Science.* 1996; 271(5247):348-350.

Janssen B J, Christodoulidou A, McCarthy A, Lambris J D, Gros P. Structure of C3b reveals conformational changes that underlie complement activity. *Nature.* 2006; 444 (7116):213-216.

Shaw C D, et al. Delineation of the complement receptor type 2-C3d complex by site-directed mutagenesis and molecular docking. *J Mol Biol.* 2010; 404(4):697-710.

Wessels M R, Butko P, Ma M, Warren H B, Lage A L, Carroll M C. Studies of group B streptococcal infection in mice deficient in complement component C3 or C4 demonstrate an essential role for complement in both innate and acquired immunity. *Proc Natl Acad Sci USA.* 1995; 92(25):11490-11494.

Li Y, Williams M E, Cousar J B, Pawluczkowycz A W, Lindorfer M A, Taylor R P. Rituximab-CD20 complexes are shaved from Z138 mantle cell lymphoma cells in intravenous and subcutaneous SCID mouse models. *J Immunol.* 2007; 179(6):4263-4271.

Strunk R C, Kunke K S, Giclas P C. Human peripheral blood monocyte-derived macrophages produce haemolytically active C3 in vitro. *Immunology.* 1983; 49(1):169-174.

Daha M R, Fearon D T, Austen K F. C3 nephritic factor (C3NeF): stabilization of fluid phase and cellbound alternative pathway convertase. *J Immunol.* 1976; 116(1):1-7.

Weiler J M, Daha M R, Austen K F, Fearon D T. Control of the amplification convertase of complement by the plasma protein beta1H. *Proc Natl Acad Sci USA.* 1976; 73(9): 3268-3272.

Pangburn M K, Schreiber R D, Muller-Eberhard H J. Human complement C3b inactivator: isolation, characterization, and demonstration of an absolute requirement for the serum protein betalH for cleavage of C3b and C4b in solution. *J Exp Med.* 1977; 146(1):257-270.

Wu J, Wu Y Q, Ricklin D, Janssen B J, Lambris J D, Gros P. Structure of complement fragment C3b-factor H and implications for host protection by complement regulators. *Nat Immunol.* 2009; 10(7):728-733.

Lyubchenko T, dal Porto J, Cambier J C, Holers V M. Coligation of the B cell receptor with complement receptor type 2 (CR2/CD21) using its natural ligand C3dg: activation without engagement of an inhibitory signaling pathway. *J Immunol.* 2005; 174(6):3264-3272.

Thurman J M, et al. A novel inhibitor of the alternative complement pathway prevents antiphospholipid antibody-induced pregnancy loss in mice. *Mol Immunol.* 2005; 42(1):87-97.

Paixao-Cavalcante D, Hanson S, Botto M, Cook H T. Pickering M C. Factor H facilitates the clearance of GBM bound iC3b by controlling C3 activation in fluid phase. *Mol Immunol.* 2009; 46(10):1942-1950.

Pickering M C, et al. Uncontrolled C3 activation causes membranoproliferative glomerulonephritis in mice deficient in complement factor H. *Nat Genet.* 2002; 31(4): 424-428.

Thurman J M, Ljubanovic D, Edelstein C L, Gilkeson G S, Holers V M. Lack of a functional alternative complement pathway ameliorates ischemic acute renal failure in mice. *J Immunol.* 2003; 170(3):1517-1523.

Renner B, et al. Binding of factor H to tubular epithelial cells limits interstitial complement activation in ischemic injury. *Kidney Int.* 2011; 80(2):165-173.

Nozaki M, et al. Drusen complement components C3a and C5a promote choroidal neovascularization. *Proc Natl Acad Sci USA.* 2006; 103(7):2328-2333.

Leveziel N, et al. Genetic factors associated with age-related macular degeneration. *Ophthalmologica.* 2011; 226(3): 87-102.

Van den Elsen J M, Isenman D E. A crystal structure of the complex between human complement receptor 2 and its ligand C3d. *Science.* 2011; 332(6029):608-611.

Sekine H, et al. The benefit of targeted and selective inhibition of the alternative complement pathway for modulating autoimmunity and renal disease in MRL/lpr mice. *Arthritis Rheum.* 2011; 63(4):1076-1085.

Song H, He C, Knaak C, Guthridge J M, Holers V M, Tomlinson S. Complement receptor 2-mediated targeting of complement inhibitors to sites of complement activation. *J Clin Invest.* 2003; 111(12):1875-1885.

Sargsyan S A, Thurman J M. Molecular imaging of autoimmune diseases and inflammation. *Mol Imaging.* 2012; 11(3):251-264.

Rother R P, Rollins S A, Mojcik C F, Brodsky R A, Bell L. Discovery and development of the complement inhibitor eculizumab for the treatment of paroxysmal nocturnal hemoglobinuria. *Nat Biotechnol.* 2007; 25(11):1256-1264.

Li K, et al. Solution structure of the complex formed between human complement C3d and full-length complement receptor type 2. *J Mol Biol.* 2008; 384(1):137-150.

Kulik L, et al. Intrinsic B cell hypo-responsiveness in mice prematurely expressing human CR2/CD21 during B cell development. *Eur J Immunol.* 2007; 37(3):623-633.

Szakonyi G, et al. Structure of the Epstein-Barr virus major envelope glycoprotein. *Nat Struct Mol Biol.* 2006; 13 (11): 996-1001.

Young K A, Chen X S, Holers V M, Hannan J P. Isolating the Epstein-Barr virus gp350/220 binding site on complement receptor type 2 (CR2/CD21). *J Biol Chem.* 2007; 282(50):36614-36625.

Young K A, Herbert A P, Barlow P N, Holers V M, Hannan J P. Molecular basis of the interaction between complement receptor type 2 (CR2/CD21) and Epstein-Barr virus glycoprotein gp350. *J Virol.* 2008; 82(22):11217-11227.

Rose K L, et al. Factor I is required for the development of membranoproliferative glomerulonephritis in factor H-deficient mice. *J Clin Invest.* 2008; 118(2):608-618.

Matsumoto M, et al. Abrogation of the alternative complement pathway by targeted deletion of murine factor B. *Proc Natl Acad Sci USA.* 1997; 94(16):8720-8725.

Kulik L, et al. Pathogenic natural antibodies recognizing annexin IV are required to develop intestinal ischemia-reperfusion injury. *J Immunol.* 2009; 182(9):5363-5373.

Hourcade D E, Wagner L M, Oglesby T J. Analysis of the short consensus repeats of human complement factor B by site-directed mutagenesis. *J Biol Chem.* 1995; 270(34): 19716-19722.

Whaley K. Measurement of complement. In: Whaley K, ed. *Methods in Complement for Clinical Immunologists.* New York, N.Y., USA: Churchill Livingstone; 1985:77-139.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for detecting a *Mycobacterium tuberculosis* (*M. tuberculosis*) infection in a subject, the method comprising:
   (a) administering to a subject an effective amount of a monoclonal antibody which binds to C3d in the subject, wherein the monoclonal antibody is conjugated to an imaging tag; and
   (b) detecting a signal generated by the imaging tag upon binding to C3d in the subject to detect the location of the *M. tuberculosis* infection in the subject.

2. The method of claim 1, wherein the monoclonal antibody comprises 3d29 or a derivative thereof.

3. The method of claim 1, wherein the monoclonal antibody binds to infected tissue in the subject.

4. The method of claim 3, wherein the infected tissue comprises inflamed tissue.

5. The method of claim 4, wherein the infected tissue is selected from the group consisting of lung, spleen, and any other extrapulmonary infected tissue.

6. The method of claim 5, wherein the monoclonal antibody co-localizes with alveolar and, peripheral phagocytes in *M. tuberculosis* infected lung sections in the subject and/or co-localizes with aggregates of macrophages in the lungs of infected subjects.

7. The method of claim 1, wherein the imaging tag is a fluorescent tag and/or a radiolabel.

8. The method of claim 1, wherein the imaging tag comprises any radioiodine nuclide.

9. The method of claim 1, wherein the imaging tag comprises $^{125}I$, $^{123}I$, $^{124}I$, or $^{131}I$.

10. The method of claim 1, wherein the imaging tag comprises LISSAMINE or a near-infrared dye with a wavelength in the range of 680-800 nm.

11. The method of claim 1, wherein the step of detecting the signal comprises performing an imaging method selected from the group consisting of computed tomography (CT), fluorescence imaging, and singe-photon emission computed tomography (SPECT), positron emission tomography (PET) and combinations thereof.

12. The method of claim 1, wherein the step of administering comprises injecting the monoclonal antibody into the subject.

13. The method of claim 12, wherein injecting comprises intravenous injection or intraperitoneal injection.

14. The method of claim 1, further comprising treating the subject for *M. tuberculosis* infection.

15. The method of claim 14, wherein treating comprises administering to the subject an effective amount of an antibiotic agent, an anti-inflammatory agent, or a combination thereof.

16. The method of claim 1, wherein the subject is human.

17. A method of treating a *M. tuberculosis* infection in a subject in need thereof, the method comprising:
   (a) administering to a subject an effective amount of a monoclonal antibody which binds to C3d, wherein the monoclonal antibody is conjugated to an imaging tag, and wherein the monoclonal antibody binds to infected tissue in the subject; and
   (b) detecting a signal generated by the imaging tag to detect the location of the *M. tuberculosis* infection in the subject; and
   (c) administering to the subject an effective amount of an antibiotic an anti-inflammatory agent, or a combination thereof.

18. The method of claim 17, wherein the infected tissue comprises inflamed tissue.

19. The method of claim 18, wherein the antibiotic agent and/or anti-inflammatory agent are administered to the location of the *M. tuberculosis* infection the subject.

20. The method of claim 17, wherein the subject is human.

21. A method for detecting a *Mycobacterium tuberculosis* (*M. tuberculosis*) infection in a subject, the method comprising:
(a) administering to a subject an effective amount of a monoclonal antibody or antibody-binding fragment thereof which binds to C3d in the subject, wherein the monoclonal antibody or antibody-binding fragment thereof is conjugated to an imaging tag; and
(b) detecting a signal generated by the imaging tag upon binding to C3d in the subject to detect the location of the *M. tuberculosis* infection in the subject wherein the monoclonal antibody or antibody-binding fragment thereof which binds to C3d in the subject is a monoclonal antibody selected from the group consisting of the following:
(i) a monoclonal antibody produced by the hybridoma cell line 3d-9a/25 deposited with the American Type Culture Collection (ATCC) as deposit number PTA-10998;
(ii) a monoclonal antibody produced by the hybridoma cell line 3d-8b/2 deposited with the ATCC as deposit number PTA-10999;
(iii) a monoclonal antibody produced by the hybridoma cell line 3d-29/5/2 deposited with the ATCC as deposit number PTA-11000;
(iv) a monoclonal antibody produced by the hybridoma cell line 3d-10/14/1 deposited with the ATCC as deposit number PTA-11010;
(v) a monoclonal antibody produced by the hybridoma cell line 3d-11/14 deposited with the ATCC as deposit number PTA-11011;
(vi) a monoclonal antibody produced by the hybridoma cell line 3d-15A9 deposited with the ATCC as deposit number PTA-11012;
(vii) a monoclonal antibody produced by the hybridoma cell line 3d-3/28/4 deposited with the ATCC as deposit number PTA-11025;
(viii) a monoclonal antibody produced by the hybridoma cell line 3d-16/3/3 deposited with the ATCC as deposit number PTA-11026; and
(ix) a monoclonal antibody produced by the hybridoma cell line 3d-31/A6/9 deposited with the ATCC as deposit number PTA-11027.

* * * * *